United States Patent [19]
Arnold

[11] Patent Number: 5,858,655
[45] Date of Patent: Jan. 12, 1999

[54] METHOD FOR DIAGNOSING NEOPLASIA BY DETECTING EXPRESSION OF PRAD1 CYCLIN

[75] Inventor: Andrew Arnold, Newton, Mass.

[73] Assignee: The General Hospital Corporation, Boston, Mass.

[21] Appl. No.: 460,694

[22] Filed: Jun. 2, 1995

Related U.S. Application Data

[62] Division of Ser. No. 667,711, Mar. 11, 1991.

[51] Int. Cl.$^6$ ........................................... C12Q 1/68
[52] U.S. Cl. .................................. 435/6; 935/78
[58] Field of Search .............................. 435/6; 536/23.1; 935/77, 78

[56] References Cited

U.S. PATENT DOCUMENTS

| | | | |
|---|---|---|---|
| 4,786,718 | 11/1988 | Weinberg et al. | 530/387 |
| 5,118,615 | 6/1992 | Matsuo et al. | 435/69.1 |
| 5,538,846 | 7/1996 | Meeker | 435/6 |

FOREIGN PATENT DOCUMENTS

| | | | |
|---|---|---|---|
| 2104871 | 9/1992 | Canada | C12N 15/12 |
| WO9215603 | 9/1992 | WIPO | C07H 21/02 |

OTHER PUBLICATIONS

Kaplan et al. (1991) Nucl. Acids Res. 19:4731–38.
Bates and Peters (Apr. 1995) Seminars in Cancer Biology 6:73–82.
Arnold et al. (1991) Cold Spring Harbor Symp. Quant. Biol. 56:93–97.
Arnold et al. (1992) Henry Ford Hospital Medical Journal 40:177–80.
Adelaide et al. (1995) Britich J. Cancer 71:64–8.
Jares et al. (1994) Cancer Res. 54:4813–17.
Nishida et al. (1994) Cancer Res. 54:3107–10.
Muller et al. (1994) Proc. Natl. Acad. Sci USA 91:2945–9.
Bosch et al. (1994) Blood 84:2726–32.
Seto et al. (1992) Oncogene 7:1401–6.
Schuuring et al. (1992) Oncogene 7:355–61.
Arnold, A., et al., "Monoclonality and Abnormal Parathyroid Hormone Genes in Parathyroid Adenomas," *New Engl. J. Med.* 318(11):658–662 (Mar. 17, 1988).
Arnold, A., et al., "Molecular Cloning and Chromosomal Mapping of DNA Rearranged With the Parathyroid Hormone Gene in a Parathyroid Adenoma," *J. Clin. Invest.* 83(6):2034–2040 (Jun. 1989).
Arnold, A., et al., "DNA Rearranged to the PTH Gene in a Parathyroid Adenoma Encodes an Abnormally Expressed Gene," *J. Bone Min. Res.* 4 (*Suppl. 1*):S262, Abstr. No. 579 (1989).
Arnold, A., in: *Molecular Genetics in Cancer Diagnosis*, Cossman, J., ed., New York: Elsevier Science Publishing Co., Inc., pp. 399–408 (1990).

Arnold, A., "Parathyroid Adenomas. Clonality in Benign Neoplasia," in: *Molecular Genetics in Cancer Diagnosis*, Cossman, J., ed., New York: Elsevier Science Publishing Co., Inc., pp. 399–408 (1990).
Bale, A.E., et al., "The Parathyroid Adenoma Breakpoint Sequence in 11q13 Maps Close to BCL1 and is not a Candidate Gene for MEN1," *Am. J. Human Genet.* 47(3):A3, Abstract No. 0002 (1990).
Cross, F.R. "DAF1, a Mutant Gene Affecting Size Control, Pheromone Arrest, and Cell Cycle Kinetics of *Saccharomyces cerevisiae*," *Molec. Cell. Biol.* 8(11):4675–4684 (Nov. 1988).
Draetta, G., et al., "Cdc2 Protein Kinase is Complexed With Both Cyclin A and B: Evidence for Proteolytic Inactivation of MPF," *Cell* 56(5):829–838 (Mar. 10, 1989).
Evans, T., et al., "Cyclin: A Protein Specified by Maternal mRNA in Sea Urchin Eggs That is Destroyed at Each Cleavage Division," *Cell* 33(2):389–396 (Jun. 1983).
Friedman, E., et al., "Genetic Abnormalities in Sporadic Parathyroid Adenomas," *J. Clin. Endocrinol. Metab.* 71(2):293–297 (Aug. 1990).
Hunt, T., "Cell Biology. Cell Cycle Gets More Cyclins," *Nature* 350:462–463 (Apr. 11, 1991).
Lew, D.J., et al., "Isolation of Three Novel Human Cyclins by Rescue of G1 Cyclin (Cln) Function in Yeast," *Cell* 66(6):1197–1206 (Sep. 20, 1991).
Matsushime, H., et al., "Colony–Stimulating Factor 1 Regulates Novel Cyclins During the G1 Phase of the Cell Cycle," *Cell* 65(4):701–713 (May 17, 1991).
Minshull, J., et al., "The A– and B–Type Cyclin Associated cdc2 Kinases in Xenopus Turn On and Off at Different Times in the Cell Cycle," *EMBO J.* 9(9):2865–2875 (Sep. 1990).
Motokura, T., et al., "A Novel Cyclin Encoded by a bcl1–Linked Candidate Oncogene," *Nature* 350:512–515 (Apr. 11, 1991).
Murray, A.W., and Kirschner, M.W., "Dominoes and Clocks: The Union of Two Views of the Cell Cycle," *Science* 246:614–621 (Nov. 3, 1989).
Nash, R., et al., "The WHI1$^+$ Gene of *Saccharomyces cerevisiae* Tethers Cell Division to Cell Size and Is a Cyclin Homolog," *EMBO J.* 7(13):4335–4346 (Dec. 20, 1988).

(List continued on next page.)

*Primary Examiner*—W. Gary Jones
*Assistant Examiner*—Amy Atzel
*Attorney, Agent, or Firm*—Sterne, Kessler, Goldstein & Fox P.L.L.C.

[57] ABSTRACT

A novel cyclin, termed prad1, is disclosed, along with the nucleic acid sequence that encodes human prad1. Antibodies that bind specifically to prad1 and cell lines and transgenic animals containing DNA that encodes prad1 are also disclosed. In addition, methods of using the antibodies or fragments of the nucleic acid sequence, for example, to diagnose a neoplastic condition by detecting expression of prad1 or to modulate cellular proliferation, are disclosed.

7 Claims, 18 Drawing Sheets

OTHER PUBLICATIONS

Nasmyth, K.A., "FAR–Reaching Discoveries About the Regulation of START," *Cell* 63(6):1117–1120 (Dec. 21, 1990).

Nurse, P., "Universal Control Mechanism Regulating Onset of M–Phase," *Nature* 344:503–508 (Apr. 5, 1990).

Pines, J., and Hunter, T., "Isolation of a Human Cyclin cDNA: Evidence for Cyclin mRNA and Protein Regulation in the Cell Cycle and for Interaction With p34cdc2," *Cell* 58(5):833–846 (Sep. 8, 1989).

Pines, J., and Hunter, T., "Human Cyclin A is Adenovirus E1A–Associated Protein p60 and Behaves Differently from Cyclin B," *Nature* 346:760–763 (Aug. 23, 1990).

Raffeld, M., and Jaffe, E.S., "bcl–1, t(11;14), and Mantle Cell–Derived Lymphomas," *Blood* 78(2):259–263 (Jul. 15, 1991).

Rosenberg, C.L., et al., "Rearrangement and Overexpression of D11S287E, a Candidate Oncogene on Chromosome 11q13 in Benign Parathyroid Tumors," *Oncogene* 6(3):449–454, BIOSIS Abstract No. 91121959 (Mar., 1991).

Rosenberg, C.L., et al., "PRAD1, a Candidate BCL1 Oncogene: Mapping and Expression in Centrocytic Lymphoma," *Proc. Natl. Acad. Sci. USA* 88(21):9638–9642, BIOSIS Abstract No. 93018797 (Nov. 1, 1991).

Sambrook, J., et al., *Molecular Cloning: A Laboratory Manual*, 2nd Ed., Cold Spring Harbor, NY: Cold Spring Harbor Laboratory Press, pp. 18.76, 18.81 (1989).

Swenson, K.I., et al., "The Clam Embryo Protein Cyclin A Induces Entry into M Phase and the Resumption of Meiosis in Xenopus Oocytes," *Cell* 47(6):861–870 (Dec. 26, 1986).

Vasicek, T.J., et al., "Nucleotide Sequence of the Human Parathyroid Hormone Gene," *Proc. Natl. Acad. Sci. USA* 80(8):2127–2131 (Apr. 1983).

Wang, J., et al., "Hepatitis B Virus Integration in a Cyclin A Gene in a Hepatocellular Carcinoma," *Nature* 343:555–557 (Feb. 8, 1990).

Westendorf, J.M., et al., "The Role of Cyclin B in Meiosis I," *J. Cell Biol.* 108(4):1431–1444 (Apr. 1989).

Withers, D.A., et al., "Characterization of a Candidate bcl–1 Gene," *Molec. Cell. Biol.* 11(10):4846–4853 (Oct. 1991).

Xiong, Y., et al., "Human D–Type Cyclin," *Cell* 65(4):691–699 (May 17, 1991).

Copy of the International Search Report for PCT Application No. PCT/US92/01925, which corresponds to US Application No. 07/667,711, the parent of the captioned application.

Copy of the Written Opinion from the International Searching Authority for PCT Application No. PCT/US92/01925, which corresponds to US Application No. 07/667,711, the parent of the captioned application.

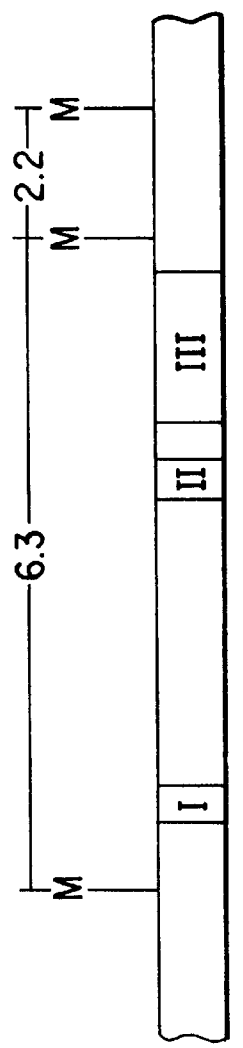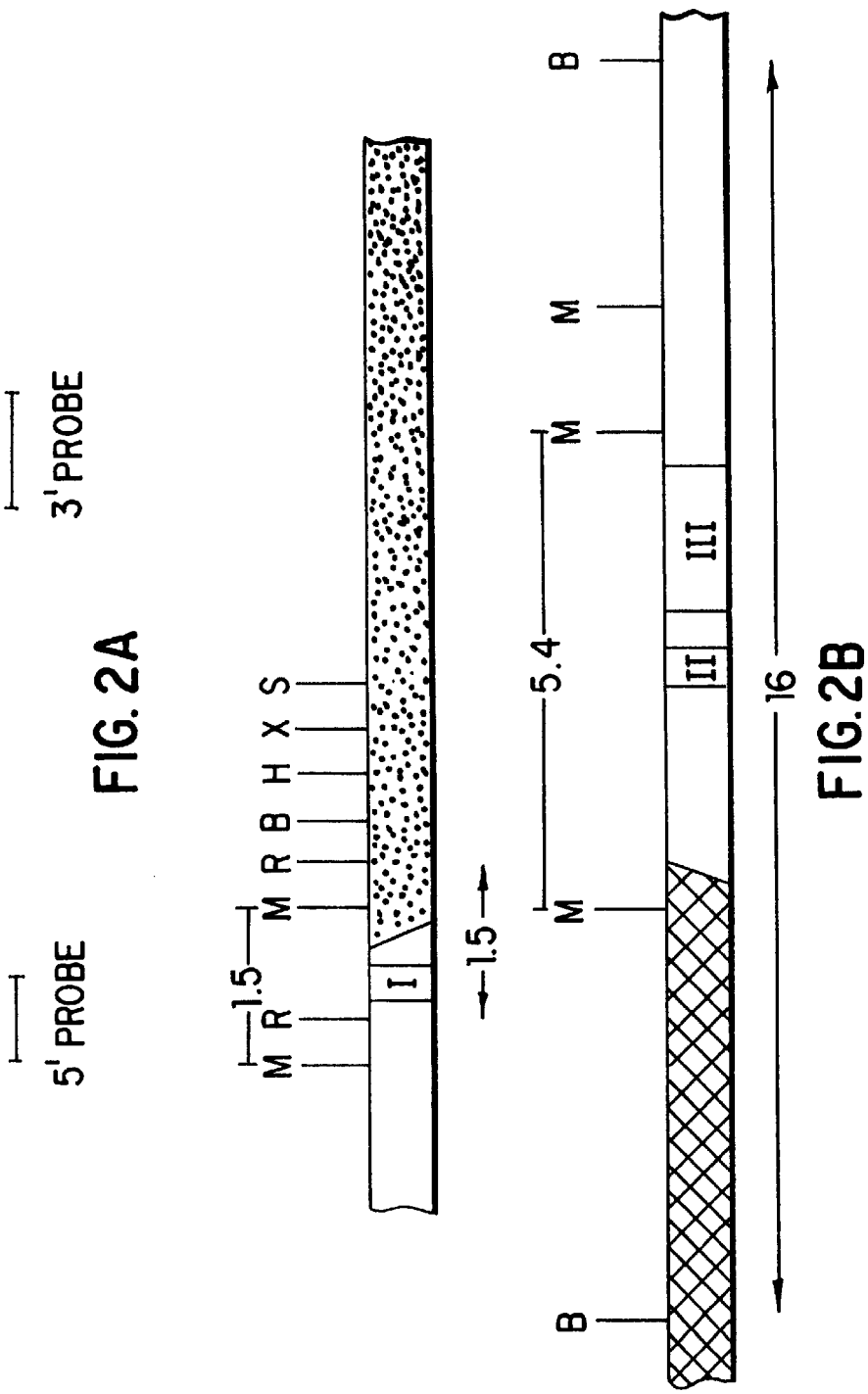
FIG. 2A
FIG. 2B

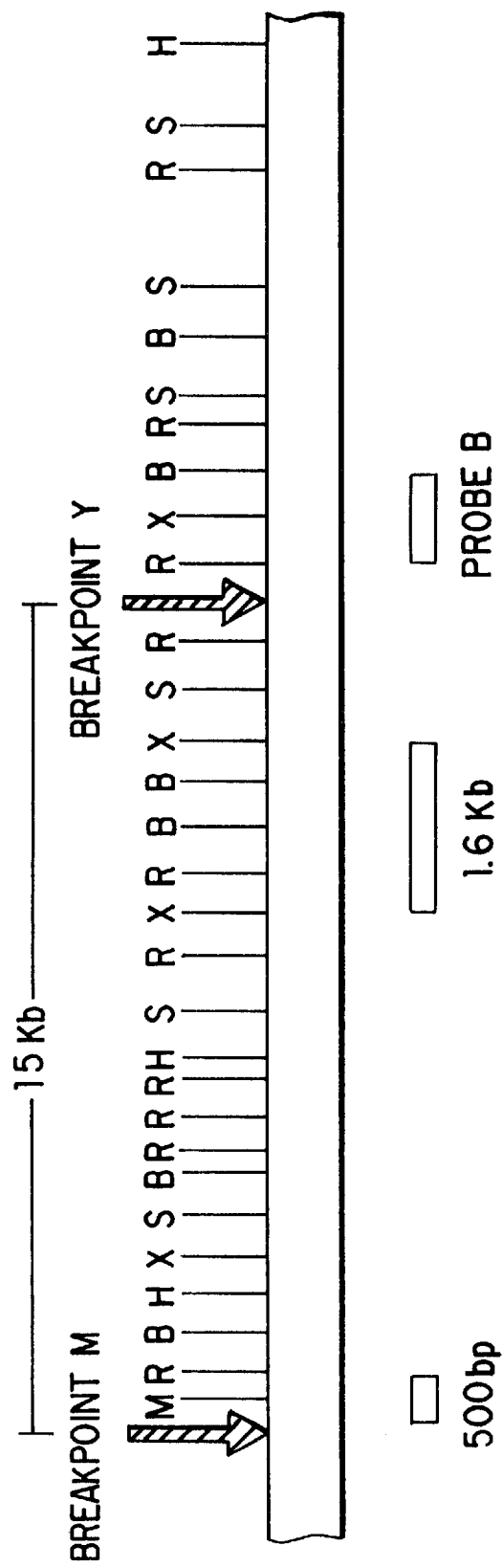

```
GGCGCAGTAG CAGGGAGCAG CAGAGTCCGC ACGCTCCGGC GAGGGGCAGA AGAGCGCGAG         60

GGAGCGCGGG GCAGCAGAAG CGAGAGCCGA GCGCGGACCC AGCCAGGACC CACAGCCCTC        120

CCCAGCTGCC CAGGAAGAGC CCCAGCC ATG GAA CAC CAG CTC CTG TGC TGC            171
                              Met Glu His Gln Leu Leu Cys Cys
                               1               5

GAA GTG GAA ACC ATC CGC GCG TAC CCC GAT GCC AAC CTC CTC AAC              219
Glu Val Glu Thr Ile Arg Ala Tyr Pro Asp Ala Asn Leu Leu Asn
         10                  15                  20

GAC CGG GTG CTG CGG GCC ATG CTG AAG GCG GAG ACC TGC GCG CCC              267
Asp Arg Val Leu Arg Ala Met Leu Lys Ala Glu Thr Cys Ala Pro
 25                  30                  35                  40

TCG GTG TCC TAC TTC AAA TGT GTG CAG AAG GAG GTC CTG CCG TCC ATG          315
Ser Val Ser Tyr Phe Lys Cys Val Gln Lys Glu Val Leu Pro Ser Met
             45                  50                  55

CGG AAG ATC GTC GCC ACC TGG ATG CTG GAG GTC TGC GAG GAA CAG AAG          363
Arg Lys Ile Val Ala Thr Trp Met Leu Glu Val Cys Glu Glu Gln Lys
         60                  65                  70

TGC GAG GAG GTC TTC CCG CTG GCC ATG AAC TAC CTG GAC CGC TTC              411
Cys Glu Glu Val Phe Pro Leu Ala Met Asn Tyr Leu Asp Arg Phe
 75                  80                  85
```

FIG.6A

```
CTG TCG CTG GAG CCC GTG AAA AAG AGC CGC CTG CAG CTG CTG GGG GCC    459
Leu Ser Leu Glu Pro Val Lys Lys Ser Arg Leu Gln Leu Leu Gly Ala
         90                  95                 100

ACT TGC ATG TTC GTG GCC TCT AAG ATG AAG GAG ACC ATC CCC CTG ACG    507
Thr Cys Met Phe Val Ala Ser Lys Met Lys Glu Thr Ile Pro Leu Thr
        105                 110                 115                 120

GCC GAG AAG CTG TGC ATC TAC ACC GAC AAC TCC ATC CGG CCC GAG GAG    555
Ala Glu Lys Leu Cys Ile Tyr Thr Asp Asn Ser Ile Arg Pro Glu Glu
        125                 130                 135

CTG CTG CAA ATG GAG CTG CTC CTG GTG CTC CTG AAC AAG CTC AAG TGG AAC CTG    603
Leu Leu Gln Met Glu Leu Leu Leu Val Leu Leu Asn Lys Leu Lys Trp Asn Leu
        140                 145                 150

GCC GCA ATG ACC CCG CAC GAT TTC ATT GAA CAC TTC CTC TTG TCC AAA ATG    651
Ala Ala Met Thr Pro His Asp Phe Ile Glu His Phe Leu Ser Lys Met
        155                 160                 165

CCA GAG GCG GAG GAG AAC AAA CAG ATC ATC CGC AAA CAC GCG CAG ACC    699
Pro Glu Ala Glu Glu Asn Lys Gln Ile Ile Arg Lys His Ala Gln Thr
        170                 175                 180

TTC GTT GCC CTC TGT GCC ACA GAT GTG AAG TTC ATT TCC AAT CCG CCC    747
Phe Val Ala Leu Cys Ala Thr Asp Val Lys Phe Ile Ser Asn Pro Pro
        185                 190                 195                 200
```

FIG. 6B

```
TCC ATG GTG GCA GCG GGG AGC GTG GTG GCC GCA GTG CAA GGC CTG AAC       795
Ser Met Val Ala Ala Gly Ser Val Val Ala Ala Val Gln Gly Leu Asn
                    205                     210                 215

CTG AGG AGC CCC AAC AAC TTC CTG TCC TAC TAC CGC CTC ACA CGC TTC       843
Leu Arg Ser Pro Asn Asn Phe Leu Ser Tyr Tyr Arg Leu Thr Arg Phe
                    220                     225                 230

CTC TCC AGA GTG ATC AAG TGT GAC CCA GAC TGC CTC CGG GCC TGC CAG       891
Leu Ser Arg Val Ile Lys Cys Asp Pro Asp Cys Leu Arg Ala Cys Gln
                    235                     240                 245

GAG CAG ATC GAA GCC CTG CTG CTG GAG TCA AGC CTG CGC CAG CAG CAG       939
Glu Gln Ile Glu Ala Leu Leu Leu Glu Ser Ser Leu Arg Gln Gln Gln
                    250                     255                 260

AAC ATG GAC CCC AAG GCC GCC GAG GAG GAA GAG GAG GAG GAG GAG GAG       987
Asn Met Asp Pro Lys Ala Ala Glu Glu Glu Glu Glu Glu Glu Glu Glu
265                     270                     275                 280

GTG GAC CTG GCT TGC ACA CCC ACC GAC GTG CGG GAC GTG GAC ATC TGA      1035
Val Asp Leu Ala Cys Thr Pro Thr Asp Val Arg Asp Val Asp Ile
                    285                     290                 295

GGGCGCCAGG CAGGCGGGCG CCACCGCCAC CCGCAGGGAG GGCGGAGCCG GCCCCAGGTG    1095

CTCCACTGAC AGTCCCTCCT CTCCGGAGCA TTTTGATACC AGAAGGGAAA GCTTCATTCT    1155
```

FIG.6C

```
CCTTGTGTTGTT GGTTGTTTTT TCCTTTGCTC TTTCCCCCTT CCATCTCTGA CTTAAGCAAA    1215

AGAAAAAGAT TACCCAAAAA CTGTCTTTAA AAGAGAGAGA GAGAAAAAAA AAATAGTATT      1275

TGCATAACCC TGAGCGGTGG GGGAGGAGGG TTGTGCTACA GATGATAGAG GATTTTATAC      1335

CCCAATAATC AACTCGTTTT TATATTAATG TACTTGTTTC TCTGTTGTAA GAATAGGCAT      1395

TAACACAAAG GAGGCGTCTC GGGAGAGGAT TAGGTTCCAT CCTTTACGTG TTTAAAAAAA      1455

AGCATAAAAA CATTTTAAAA ACATAGAAAA ATTCAGCAAA CCATTTTTAA AGTAGAAGAG      1515

GGTTTTAGGT AGAAAAACAT ATTCTTGTGC TTTTCCTGAT AAAGCACAGC TGTAGTGGGG      1575

TTCTAGGCAT CTCTGTACTT TGCTTGCTCA TATGCATGTA GTCACTTTAT AAGTCATTGT      1635

ATGTTATTAT ATTCCGTAGG TAGATGTGTA ACCTCTTCAC CTTATTCATG GCTGAAGTCA      1695

CCTCTTGGTT ACAGTAGCGT AGCGTGGCCG TGTGCATGTC CTTTGGCGCCT GTGACCACCA     1755

CCCCAACAAA CCATCCAGTG ACAAACCATC CAGTGGAGGT TTGTCGGGCA CCAGCCAGCG      1815

TAGCAGGGTC GGGAAAGGCC ACCTGTCCCA CTCCTACGAT ACGCTACTAT AAAGAGAAGA      1875

CGAAATAGTG ACATAATATA TTCTATTTTT ATACTCTTCC TATTTTTGTA GTGACCTGTT      1935

TATGAGATGC TGGTTTTCTA CCCAACGGCC CTGCAGCCAG CTCACGTCCA GGTTCAACCC      1995
```

FIG.6D

```
ACAGCTACTT GGTTTGTGTT CTTCTTCATA TTCTAAAACC ATTCCATTTC CAAGCACTTT   2055

CAGTCCAATA GGTGTAGGAA ATAGCGCTGT TTTTGTTGTG TGTGCAGGGA GGGCAGTTTT   2115

CTAATGGAAT GGTTTGGGAA TATCCATGTA CTTGTTTGCA AGCAGGACTT TGAGGCAAGT   2175

GTGGGCCACT GTGGTGGCAG TGGAGGTGGG GTGTTTGGGA GGCTGCGTGC CAGTCAAGAA   2235

GAAAAAGGTT TGCATTCTCA CATTGCCAGG ATGATAAGTT CCTTTCCTTT TCTTTAAAGA   2295

AGTTGAAGTT TAGGAATCCT TTGGTGCCAA CTGGTGTTTG AAAGTAGGGA CCTCAGAGGT   2355

TTACCTAGAG AACAGGTGGT TTTTAAGGGT TATCTTAGAT GTTTCACACC GGAAGGTTTT   2415

TAAACACTAA AATATATAAT TTATAGTTAA GGCTAAAAAG TATATTTATT GCAGAGGATG   2475

TTCATAAGGC CAGTATGATT TATAAATGCA ATCTCCCCTT GATTTAAACA CACAGATACA   2535

CACACACACA CACACACACA CACAAACCTT CTGCCTTTGA TGTTACAGAT TTAATACAGT   2595

TTATTTTTAA AGATAGATCC TTTTATAGGT GAGAAAAAAA CAATCTGGAA GAAAAAAACC   2655

ACACAAAGAC ATTGATTCAG CCTGTTTGGC GTTTCCCAGA GTCATCTGAT TGGACAGGCA   2715

TGGGTGCAAG GAAAATTAGG GTACTCAACC TAAGTTCGGT TCCGATGAAT TCTTATCCCC   2775

TGCCCCTTCC TTTAAAAAAC TTAGTGACAA AATAGACAAT TTGCACATCT TGGCTATGTA   2835
```

FIG.6E

```
ATTCTTGTAA TTTTTATTTA GGAAGTGTTG AAGGGAGGTG GCAAGAGTGT GGAGGCTGAC   2895

GTGTGAGGGA GGACAGGGCGG GAGGAGGTGT GAGGAGGAGG CTCCCGAGGG GAAGGGGCGG   2955

TGCCCACACC GGGGACAGGC CGCAGCTCCA TTTTCTTATT GCGCTGCTAC CGTTGACTTC   3015

CAGGCACGGT TTGGAAATAT TCACATCGCT TCTGTGTATC TCTTTCACAT TGTTTGCTGC   3075

TATTGGAGGA TCAGTTTTTT GTTTTACAAT GTCATATACT GCCATGTACT AGTTTTAGTT   3135

TTCTCTTAGA ACATTGTATT ACAGATGCCT TTTTTGTAGT TTTTTTTTTT TTTATGTGAT   3195

CAATTTTGAC TTAATGTGAT TACTGCTCTA TTCCAAAAAG GTTGCTGTTT CACAATACCT   3255

CATGCTTCAC TTAGCCATGG TGGACCCAGC GGGCAGGTTC TGCCTGCTTT GGCGGGCAGA   3315

CACGCGGGCG CGATCCCACA CAGGCTGGCG GGGGCCGGCC CCGAGGCCGC GTGCGTGAGA   3375

ACCGCGCCGG TGTCCCCAGA GACCAGGCTG TGTCCCTCTT CTCTTCCCTG CGCCTGTGAT   3435

GCTGGGCACT TCATCTGATC GGGGGCGTAG CATCATAGTA GTTTTTACAG CTGTGTTATW   3495

CTTTGCGTGT AGCTATGGAA GTTGCATAAT TATTATTATT ATTATTATAA CAAGTGTGTC   3555

TTACGTGCCA CCACGGCGTT GTACCTGTAG GACTCTCATT CGGGATGATT GGAATAGCTT   3615

CTGGAATTTG TTCAAGTTTT GGGTATGTTT AATCTGTTAT GTACTAGTGT TCTGTTTGTT   3675
```

FIG.6F

```
ATTGTTTTGT TAATTACACC ATAATGCTAA TTTAAAGAGA CTCCAAATCT CAATGAAGCC    3735

AGCTCACAGT GCTGTGTGCC CCGGTCACCT AGCAAGCTGC CGAACCAAAA GAATTTGCAC    3795

CCCGCTGCGG GCCCACGTGG TTGGGGCCCT GCCCTGGCAG GGTCATCCTG TGCTCGGAGG    3855

CCATCTCGGG CACAGGCCCA CCCCGCCCCA CCCCTCCAGA ACACGGCTCA CGCTTACCTC    3915

AACCATCCTG GCTGCGGGCGT CTGTCTGAAC CAAGTCCTGG CCTTGAGGGA CGCTTTGTCT    3975

GTCGTGATGG GGCAAGGGCA AGGGAGTCT ATGTTGTGTG TRTCGAGAGG CCAAAGGCTG    4035

GTGGCAAGTG CACGGGGCAC AGGGAGTCT GTCCTGTGAC GCGCAAGTCT GAGGGTCTGG    4095

GCGGGCGGGCG GCTGGGTCTG TGCATTTCTG GTTGCACCGC GGGCGTTCCC AGCACCAACA    4155

TGTAACCGGC ATGTTTCCAG CAGAAGACAA AAAGACAAAC ATGAAAGTCT AGAAATAAAA    4215

CTGGTAAAAC CCCAAAAAAA AAAAAAAAAA                                     4244
```

FIG. 6G

| | | |
|---|---|---|
| human cyclin A: | MRAILVDWLVEVGEEYKLQNETLHLAVNYIDRFLSSMSVLRGKLQLVGTAAMLLASKFEEIYPPEVAEFVYITDDTYTK | 288 |
| | ||| |***|||| | ||*|*||| | *| ***||||*|* | *||| | ||** | |
| prad1: | MRKIVATWMLEVCEEEQKCEEEVFPLAMNYLDRFLSLEPVKKSRLQLLGATCMFVASKMKETIPLTAEKLCIYTDNSIRP | 134 |
| | ||*|***|||*| |**||||*|* | |**|*||||| *| |***||||| | | |*|*| | || ||** * | |
| clam cyclin A: | MRCILVDWLVEVSEEDKLHRETLFLGVNYIDRFLSKISVLRGKLQLVGAASMFLAAKYEEIYPPDVKEFAYITDDTYTS | 273 |

| | | |
|---|---|---|
| human cyclin A: | KQVLRMEHLVLKVLTFDLAAPTVNQFLTQYFLHQQPANCKVESL....AMFLGELSLIDADPYLKYLPSVIAGAA | 359 |
| | **|||**|*||**|||| |* * * * ||| | ***|*** | |
| prad1: | EELLQMELLLVNKLKWNLAAMTPHDFIEHFLSKMPEAEENKQIIRKHAQTFVALCATDVK.FISNPPSMVAAGS | 207 |
| | ***|||**| |***|||| ** *  |* ** || |***| | |
| clam cyclin A: | QQVLRMEHLILKVLTFDVAVPTTNWFCEDFL.KSCDADDK...LKSLTMFLTELTLIDMDAYLKYLPSITAAAA | 343 |

| | | |
|---|---|---|
| human cyclin B: | MRAILIDWLVQVQMKFRLLQETMYMTVSIIDRFMQNNCVPKKMLQLVGVTAMFIASKYEEMYPPEIGDFAFVTDNTYTK | 279 |
| | ||*| ||*||**| | *** *||* | |**|*|||| | || *| | |
| prad1: | MRKIVATWMLEVCEEEQKCEEEVFPLAMNYLDRFLSLEPVKKSRLQLLGATCMFVASKMKETIPLTAEKLCIYTDNSIRP | 134 |
| | ||*|***|* | * ||||*|* |***||||| *|||* * *||||| |* * *| *| | |
| cdc13: | MRGILTDWLIEVHSRFRLLPETLFLAVNIIDRFLSLRVCSLNKLQLVGIAALFIASKYEEVMCPSVQNFVYMADGGYDE | 313 |

| | | |
|---|---|---|
| human cyclin B: | HQIRQMEMKILRALNFGLGRPLPLHFLRR.ASKIGEVDVEQHTL...AKYLMELTMLDYDMVHFPPSQIAAGA | 348 |
| | ** ||*** |*  ||**| |* ||*** * | * | | |
| prad1: | EELLQMELLLVNKLKWNLAAMTPHDFIEHFLSKMPEAEENKQIIRKHAQTFVALCATDVKFISNPPSMVAAGS | 207 |
| | |*|||  |* * |||  * *** |* || *** | || |*** || || |** | |
| cdc13: | EEILQAERYILRVLEFNLAYPNPMN....FLRRISKADFYDIQTRTVAKYLVEIGLLDHKLLPYPPSQQCAAA | 382 |

| | | |
|---|---|---|
| prad1: | MRKIVATWMLEVCEEEQKCEEEVFPLAMNYLDRFLSLEPVKKSRLQLLGATCMFVASKMKETIPLTA......EKLCIYTD | 129 |
| | || *** |* ||** | |* ||*** *| ||| **** || | ||||**|| * | |
| cln3: | MRFLIFDFIMYCHTRLNLSTSTLFLTFTILDKYSSRFIIKSYNVQLLSLTALWISSKFWDSKNRMATLKVLQNLC.CNQ | 184 |

| | | |
|---|---|---|
| prad1: | NSIRPEELLQMELLLVNKLKWNLAAMTPHD.FIEHFLSKMPEAEENKQIIRKHAQTFVALCATDVKFISNPPSMVAAGS | 207 |
| | ||*  |* |||* | ||| ||| ** |*|*||  |**  *** * | |
| cln3: | YSIK..QFTTMEMHLFKSLDWSICQSATFDSYIDIFLFQSTSPLSPGVVL...SAPLEAFIQQKLALLNNAAGTAINKS | 258 |

FIG. 7

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 4244 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 148..1035

( x i ) SEQUENCE DESCRIPTION: SEQ ID NO:1:

```
GGCGCAGTAG  CAGCGAGCAG  CAGAGTCCGC  ACGCTCCGGC  GAGGGGCAGA  AGAGCGCGAG        60

GGAGCGCGGG  GCAGCAGAAG  CGAGAGCCGA  GCGCGGACCC  AGCCAGGACC  CACAGCCCTC       120

CCCAGCTGCC  CAGGAAGAGC  CCCAGCC ATG GAA CAC CAG CTC CTG TGC TGC              171
                                Met Glu His Gln Leu Leu Cys Cys
```

```
                            1                   5
GAA GTG GAA ACC ATC CGC CGC GCG TAC CCC GAT GCC AAC CTC CTC AAC    219
Glu Val Glu Thr Ile Arg Arg Ala Tyr Pro Asp Ala Asn Leu Leu Asn
     10              15                  20

GAC CGG GTG CTG CGG GCC ATG CTG AAG GCG GAG GAG ACC TGC GCG CCC    267
Asp Arg Val Leu Arg Ala Met Leu Lys Ala Glu Glu Thr Cys Ala Pro
 25              30                  35                      40

TCG GTG TCC TAC TTC AAA TGT GTG CAG AAG GAG GTC CTG CCG TCC ATG    315
Ser Val Ser Tyr Phe Lys Cys Val Gln Lys Glu Val Leu Pro Ser Met
                 45                  50                  55

CGG AAG ATC GTC GCC ACC TGG ATG CTG GAG GTC TGC GAG GAA CAG AAG    363
Arg Lys Ile Val Ala Thr Trp Met Leu Glu Val Cys Glu Glu Gln Lys
             60                  65                  70

TGC GAG GAG GAG GTC TTC CCG CTG GCC ATG AAC TAC CTG GAC CGC TTC    411
Cys Glu Glu Glu Val Phe Pro Leu Ala Met Asn Tyr Leu Asp Arg Phe
         75                  80                  85

CTG TCG CTG GAG CCC GTG AAA AAG AGC CGC CTG CAG CTG CTG GGG GCC    459
Leu Ser Leu Glu Pro Val Lys Lys Ser Arg Leu Gln Leu Leu Gly Ala
     90                  95                 100

ACT TGC ATG TTC GTG GCC TCT AAG ATG AAG GAG ACC ATC CCC CTG ACG    507
Thr Cys Met Phe Val Ala Ser Lys Met Lys Glu Thr Ile Pro Leu Thr
105                 110                 115                 120

GCC GAG AAG CTG TGC ATC TAC ACC GAC AAC TCC ATC CGG CCC GAG GAG    555
Ala Glu Lys Leu Cys Ile Tyr Thr Asp Asn Ser Ile Arg Pro Glu Glu
             125                 130                 135

CTG CTG CAA ATG GAG CTG CTC CTG GTG AAC AAG CTC AAG TGG AAC CTG    603
Leu Leu Gln Met Glu Leu Leu Leu Val Asn Lys Leu Lys Trp Asn Leu
         140                 145                 150

GCC GCA ATG ACC CCG CAC GAT TTC ATT GAA CAC TTC CTC TCC AAA ATG    651
Ala Ala Met Thr Pro His Asp Phe Ile Glu His Phe Leu Ser Lys Met
     155                 160                 165

CCA GAG GCG GAG GAG AAC AAA CAG ATC ATC CGC AAA CAC GCG CAG ACC    699
Pro Glu Ala Glu Glu Asn Lys Gln Ile Ile Arg Lys His Ala Gln Thr
170                 175                 180

TTC GTT GCC CTC TGT GCC ACA GAT GTG AAG TTC ATT TCC AAT CCG CCC    747
Phe Val Ala Leu Cys Ala Thr Asp Val Lys Phe Ile Ser Asn Pro Pro
185                 190                 195                 200

TCC ATG GTG GCA GCG GGG AGC GTG GTG GCC GCA GTG CAA GGC CTG AAC    795
Ser Met Val Ala Ala Gly Ser Val Val Ala Ala Val Gln Gly Leu Asn
             205                 210                 215

CTG AGG AGC CCC AAC AAC TTC CTG TCC TAC TAC CGC CTC ACA CGC TTC    843
Leu Arg Ser Pro Asn Asn Phe Leu Ser Tyr Tyr Arg Leu Thr Arg Phe
         220                 225                 230

CTC TCC AGA GTG ATC AAG TGT GAC CCA GAC TGC CTC CGG GCC TGC CAG    891
Leu Ser Arg Val Ile Lys Cys Asp Pro Asp Cys Leu Arg Ala Cys Gln
     235                 240                 245

GAG CAG ATC GAA GCC CTG CTG GAG TCA AGC CTG CGC CAG GCC CAG CAG    939
Glu Gln Ile Glu Ala Leu Leu Glu Ser Ser Leu Arg Gln Ala Gln Gln
250                 255                 260

AAC ATG GAC CCC AAG GCC GCC GAG GAG GAG GAA GAG GAG GAG GAG GAG    987
Asn Met Asp Pro Lys Ala Ala Glu Glu Glu Glu Glu Glu Glu Glu Glu
265                 270                 275                 280

GTG GAC CTG GCT TGC ACA CCC ACC GAC GTG CGG GAC GTG GAC ATC TGA    1035
Val Asp Leu Ala Cys Thr Pro Thr Asp Val Arg Asp Val Asp Ile
             285                 290                 295

GGGCGCCAGG CAGGCGGGCG CCACCGCCAC CCGCAGCGAG GCGGAGCCG GCCCCAGGTG    1095
CTCCACTGAC AGTCCCTCCT CTCCGGAGCA TTTTGATACC AGAAGGGAAA GCTTCATTCT    1155
CCTTGTTGTT GGTTGTTTTT TCCTTTGCTC TTTCCCCCTT CCATCTCTGA CTTAAGCAAA    1215
```

```
AGAAAAAGAT  TACCCAAAAA  CTGTCTTTAA  AAGAGAGAGA  GAGAAAAAAA  AAATAGTATT   1275
TGCATAACCC  TGAGCGGTGG  GGGAGGAGGG  TTGTGCTACA  GATGATAGAG  GATTTTATAC   1335
CCCAATAATC  AACTCGTTTT  TATATTAATG  TACTTGTTTC  TCTGTTGTAA  GAATAGGCAT   1395
TAACACAAAG  GAGGCGTCTC  GGGAGAGGAT  TAGGTTCCAT  CCTTTACGTG  TTTAAAAAAA   1455
AGCATAAAAA  CATTTTAAAA  ACATAGAAAA  ATTCAGCAAA  CCATTTTAA   AGTAGAAGAG   1515
GGTTTTAGGT  AGAAAAACAT  ATTCTTGTGC  TTTTCCTGAT  AAAGCACAGC  TGTAGTGGGG   1575
TTCTAGGCAT  CTCTGTACTT  TGCTTGCTCA  TATGCATGTA  GTCACTTTAT  AAGTCATTGT   1635
ATGTTATTAT  ATTCCGTAGG  TAGATGTGTA  ACCTCTTCAC  CTTATTCATG  GCTGAAGTCA   1695
CCTCTTGGTT  ACAGTAGCGT  AGCGTGGCCG  TGTGCATGTC  CTTTGCGCCT  GTGACCACCA   1755
CCCCAACAAA  CCATCCAGTG  ACAAACCATC  CAGTGGAGGT  TTGTCGGGCA  CCAGCCAGCG   1815
TAGCAGGGTC  GGGAAAGGCC  ACCTGTCCCA  CTCCTACGAT  ACGCTACTAT  AAAGAGAAGA   1875
CGAAATAGTG  ACATAATATA  TTCTATTTTT  ATACTCTTCC  TATTTTTGTA  GTGACCTGTT   1935
TATGAGATGC  TGGTTTTCTA  CCCAACGGCC  CTGCAGCCAG  CTCACGTCCA  GGTTCAACCC   1995
ACAGCTACTT  GGTTTGTGTT  CTTCTTCATA  TTCTAAAACC  ATTCCATTTC  CAAGCACTTT   2055
CAGTCCAATA  GGTGTAGGAA  ATAGCGCTGT  TTTTGTTGTG  TGTGCAGGGA  GGGCAGTTTT   2115
CTAATGGAAT  GGTTTGGGAA  TATCCATGTA  CTTGTTTGCA  AGCAGGACTT  TGAGGCAAGT   2175
GTGGGCCACT  GTGGTGGCAG  TGGAGGTGGG  GTGTTTGGGA  GGCTGCGTGC  CAGTCAAGAA   2235
GAAAAGGTT   TGCATTCTCA  CATTGCCAGG  ATGATAAGTT  CCTTTCCTTT  TCTTTAAAGA   2295
AGTTGAAGTT  TAGGAATCCT  TTGGTGCCAA  CTGGTGTTTG  AAAGTAGGGA  CCTCAGAGGT   2355
TTACCTAGAG  AACAGGTGGT  TTTTAAGGGT  TATCTTAGAT  GTTTCACACC  GGAAGGTTTT   2415
TAAACACTAA  AATATATAAT  TTATAGTTAA  GGCTAAAAAG  TATATTTATT  GCAGAGGATG   2475
TTCATAAGGC  CAGTATGATT  TATAAATGCA  ATCTCCCCTT  GATTAAACA   CACAGATACA   2535
CACACACACA  CACACACACA  CACAAACCTT  CTGCCTTTGA  TGTTACAGAT  TAATACAGT    2595
TTATTTTTAA  AGATAGATCC  TTTTATAGGT  GAGAAAAAAA  CAATCTGGAA  GAAAAAAACC   2655
ACACAAAGAC  ATTGATTCAG  CCTGTTTGGC  GTTTCCCAGA  GTCATCTGAT  TGGACAGGCA   2715
TGGGTGCAAG  GAAAATTAGG  GTACTCAACC  TAAGTTCGGT  TCCGATGAAT  TCTTATCCCC   2775
TGCCCCTTCC  TTTAAAAAAC  TTAGTGACAA  AATAGACAAT  TTGCACATCT  TGGCTATGTA   2835
ATTCTTGTAA  TTTTTATTTA  GGAAGTGTTG  AAGGGAGGTG  GCAAGAGTGT  GGAGGCTGAC   2895
GTGTGAGGGA  GGACAGGCGG  GAGGAGGTGT  GAGGAGGAGG  CTCCCGAGGG  GAAGGGGCGG   2955
TGCCCACACC  GGGGACAGGC  CGCAGCTCCA  TTTTCTTATT  GCGCTGCTAC  CGTTGACTTC   3015
CAGGCACGGT  TTGGAAATAT  TCACATCGCT  TCTGTGTATC  TCTTTCACAT  TGTTTGCTGC   3075
TATTGGAGGA  TCAGTTTTTT  GTTTTACAAT  GTCATATACT  GCCATGTACT  AGTTTTAGTT   3135
TTCTCTTAGA  ACATTGTATT  ACAGATGCCT  TTTTGTAGT   TTTTTTTTT   TTTATGTGAT   3195
CAATTTTGAC  TTAATGTGAT  TACTGCTCTA  TTCCAAAAG   GTTGCTGTTT  CACAATACCT   3255
CATGCTTCAC  TTAGCCATGG  TGGACCCAGC  GGGCAGGTTC  TGCCTGCTTT  GGCGGGCAGA   3315
CACGCGGGCG  CGATCCCACA  CAGGCTGGCG  GGGGCCGGCC  CCGAGGCCGC  GTGCGTGAGA   3375
ACCGCGCCGG  TGTCCCCAGA  GACCAGGCTG  TGTCCCTCTT  CTCTTCCCTG  CGCCTGTGAT   3435
GCTGGGCACT  TCATCTGATC  GGGGGCGTAG  CATCATAGTA  GTTTTTACAG  CTGTGTTATW   3495
CTTTGCGTGT  AGCTATGGAA  GTTGCATAAT  TATTATTAT   ATTATTATAA  CAAGTGTGTC   3555
TTACGTGCCA  CCACGGCGTT  GTACCTGTAG  GACTCTCATT  CGGGATGATT  GGAATAGCTT   3615
```

```
CTGGAATTTG TTCAAGTTTT GGGTATGTTT AATCTGTTAT GTACTAGTGT TCTGTTTGTT    3675
ATTGTTTTGT TAATTACACC ATAATGCTAA TTTAAAGAGA CTCCAAATCT CAATGAAGCC    3735
AGCTCACAGT GCTGTGTGCC CCGGTCACCT AGCAAGCTGC CGAACCAAAA GAATTTGCAC    3795
CCCGCTGCGG GCCCACGTGG TTGGGGCCCT GCCCTGGCAG GGTCATCCTG TGCTCGGAGG    3855
CCATCTCGGG CACAGGCCCA CCCCGCCCCA CCCCTCCAGA ACACGGCTCA CGCTTACCTC    3915
AACCATCCTG GCTGCGGCGT CTGTCTGAAC CACGCGGGGG CCTTGAGGGA CGCTTTGTCT    3975
GTCGTGATGG GGCAAGGGCA CAAGTCCTGG ATGTTGTGTG TRTCGAGAGG CCAAAGGCTG    4035
GTGGCAAGTG CACGGGGCAC AGCGGAGTCT GTCCTGTGAC GCGCAAGTCT GAGGGTCTGG    4095
GCGGCGGGCG GCTGGGTCTG TGCATTTCTG GTTGCACCGC GGCGCTTCCC AGCACCAACA    4155
TGTAACCGGC ATGTTTCCAG CAGAAGACAA AAAGACAAAC ATGAAAGTCT AGAAATAAAA    4215
CTGGTAAAAC CCCAAAAAAA AAAAAAAA                                      4244
```

(2) INFORMATION FOR SEQ ID NO:2:

(i) SEQUENCE CHARACTERISTICS:
        (A) LENGTH: 295 amino acids
        (B) TYPE: amino acid
        (D) TOPOLOGY: linear (ii) MOLECULE TYPE: protein (xi) SEQUENCE DESCRIPTION: SEQ ID NO:2:

```
Met Glu His Gln Leu Leu Cys Cys Glu Val Glu Thr Ile Arg Arg Ala
 1               5                  10                  15
Tyr Pro Asp Ala Asn Leu Leu Asn Asp Arg Val Leu Arg Ala Met Leu
                20                  25                  30
Lys Ala Glu Glu Thr Cys Ala Pro Ser Val Ser Tyr Phe Lys Cys Val
            35                  40                  45
Gln Lys Glu Val Leu Pro Ser Met Arg Lys Ile Val Ala Thr Trp Met
        50                  55                  60
Leu Glu Val Cys Glu Glu Gln Lys Cys Glu Glu Glu Val Phe Pro Leu
65                  70                  75                  80
Ala Met Asn Tyr Leu Asp Arg Phe Leu Ser Leu Glu Pro Val Lys Lys
                85                  90                  95
Ser Arg Leu Gln Leu Leu Gly Ala Thr Cys Met Phe Val Ala Ser Lys
               100                 105                 110
Met Lys Glu Thr Ile Pro Leu Thr Ala Glu Lys Leu Cys Ile Tyr Thr
               115                 120                 125
Asp Asn Ser Ile Arg Pro Glu Glu Leu Leu Gln Met Glu Leu Leu Leu
           130                 135                 140
Val Asn Lys Leu Lys Trp Asn Leu Ala Ala Met Thr Pro His Asp Phe
145                 150                 155                 160
Ile Glu His Phe Leu Ser Lys Met Pro Glu Ala Glu Glu Asn Lys Gln
               165                 170                 175
Ile Ile Arg Lys His Ala Gln Thr Phe Val Ala Leu Cys Ala Thr Asp
               180                 185                 190
Val Lys Phe Ile Ser Asn Pro Pro Ser Met Val Ala Ala Gly Ser Val
           195                 200                 205
Val Ala Ala Val Gln Gly Leu Asn Leu Arg Ser Pro Asn Asn Phe Leu
           210                 215                 220
Ser Tyr Tyr Arg Leu Thr Arg Phe Leu Ser Arg Val Ile Lys Cys Asp
225                 230                 235                 240
Pro Asp Cys Leu Arg Ala Cys Gln Glu Gln Ile Glu Ala Leu Leu Glu
```

|  |  |  |  |  | 245 |  |  |  |  | 250 |  |  |  |  | 255 |
|--|--|--|--|--|--|--|--|--|--|--|--|--|--|--|--|

Ser Ser Leu Arg Gln Ala Gln Gln Asn Met Asp Pro Lys Ala Ala Glu
              260                 265                 270

Glu Glu Glu Glu Glu Glu Glu Glu Val Asp Leu Ala Cys Thr Pro Thr
            275                 280                 285

Asp Val Arg Asp Val Asp Ile
290                 295

(2) INFORMATION FOR SEQ ID NO:3:

(i) SEQUENCE CHARACTERISTICS:
        (A) LENGTH: 150 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:3:

Met Arg Ala Ile Leu Val Asp Trp Leu Val Glu Val Gly Glu Glu Tyr
 1               5                  10                  15

Lys Leu Gln Asn Glu Thr Leu His Leu Ala Val Asn Tyr Ile Asp Arg
              20                  25                  30

Phe Leu Ser Ser Met Ser Val Leu Arg Gly Lys Leu Gln Leu Val Gly
            35                  40                  45

Thr Ala Ala Met Leu Leu Ala Ser Lys Phe Glu Glu Ile Tyr Pro Pro
          50                  55                  60

Glu Val Ala Glu Phe Val Tyr Ile Thr Asp Asp Thr Tyr Thr Lys Lys
 65                 70                  75                  80

Gln Val Leu Arg Met Glu His Leu Val Leu Lys Val Leu Thr Phe Asp
                85                  90                  95

Leu Ala Ala Pro Thr Val Asn Gln Phe Leu Thr Gln Tyr Phe Leu His
                100                 105                 110

Gln Gln Pro Ala Asn Cys Lys Val Glu Ser Leu Ala Met Phe Leu Gly
            115                 120                 125

Glu Leu Ser Leu Ile Asp Ala Asp Pro Tyr Leu Lys Tyr Leu Pro Ser
          130                 135                 140

Val Ile Ala Gly Ala Ala
145                 150

(2) INFORMATION FOR SEQ ID NO:4:

(i) SEQUENCE CHARACTERISTICS:
        (A) LENGTH: 152 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:4:

Met Arg Lys Ile Val Ala Thr Trp Met Leu Glu Val Cys Glu Glu Gln
 1               5                  10                  15

Lys Cys Glu Glu Glu Val Phe Pro Leu Ala Met Asn Tyr Leu Asp Arg
              20                  25                  30

Phe Leu Ser Leu Glu Pro Val Lys Lys Ser Arg Leu Gln Leu Leu Gly
            35                  40                  45

Ala Thr Cys Met Phe Val Ala Ser Lys Met Lys Glu Thr Ile Pro Leu
          50                  55                  60

Thr Ala Glu Lys Leu Cys Ile Tyr Thr Asp Asn Ser Ile Arg Pro Glu

```
                65                         70                           75                            80
            Glu   Leu   Leu   Gln   Met   Glu   Leu   Leu   Val   Asn   Lys   Leu   Lys   Trp   Asn
                              85                      90                              95

Leu   Ala   Ala   Met   Thr   Pro   His   Asp   Phe   Ile   Glu   His   Phe   Leu   Ser   Lys
                              100                    105                              110

Met   Pro   Glu   Ala   Glu   Glu   Asn   Lys   Gln   Ile   Ile   Arg   Lys   His   Ala   Gln
                              115                   120                               125

Thr   Phe   Val   Ala   Leu   Cys   Ala   Thr   Asp   Val   Lys   Phe   Ile   Ser   Asn   Pro
                  130                           135                               140

Pro   Ser   Met   Val   Ala   Ala   Gly   Ser
            145                           150
```

( 2 ) INFORMATION FOR SEQ ID NO:5:

( i ) SEQUENCE CHARACTERISTICS:
        ( A ) LENGTH: 149 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:5:

```
            Met   Arg   Cys   Ile   Leu   Val   Asp   Trp   Leu   Val   Glu   Val   Ser   Glu   Glu   Asp
            1                       5                         10                              15

Lys   Leu   His   Arg   Glu   Thr   Leu   Phe   Leu   Gly   Val   Asn   Tyr   Ile   Asp   Arg
                              20                      25                              30

Phe   Leu   Ser   Lys   Ile   Ser   Val   Leu   Arg   Gly   Lys   Leu   Gln   Leu   Val   Gly
                              35                      40                              45

Ala   Ala   Ser   Met   Phe   Leu   Ala   Ala   Lys   Tyr   Glu   Glu   Ile   Tyr   Pro   Pro
                  50                            55                                60

Asp   Val   Lys   Glu   Phe   Ala   Tyr   Ile   Thr   Asp   Asp   Thr   Tyr   Thr   Ser   Gln
            65                            70                            75                            80

Gln   Val   Leu   Arg   Met   Glu   His   Leu   Ile   Leu   Lys   Val   Leu   Thr   Phe   Asp
                              85                      90                              95

Val   Ala   Val   Pro   Thr   Thr   Asn   Trp   Phe   Cys   Glu   Asp   Phe   Leu   Lys   Ser
                              100                     105                             110

Cys   Asp   Ala   Asp   Asp   Lys   Leu   Lys   Ser   Leu   Thr   Met   Phe   Leu   Thr   Glu
                              115                     120                             125

Leu   Thr   Leu   Ile   Asp   Met   Asp   Ala   Tyr   Leu   Lys   Tyr   Leu   Pro   Ser   Ile
                  130                           135                             140

Thr   Ala   Ala   Ala   Ala
            145
```

( 2 ) INFORMATION FOR SEQ ID NO:6:

( i ) SEQUENCE CHARACTERISTICS:
        ( A ) LENGTH: 148 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:6:

```
            Met   Arg   Ala   Ile   Leu   Ile   Asp   Trp   Leu   Val   Gln   Val   Gln   Met   Lys   Phe
            1                       5                         10                              15

Arg   Leu   Leu   Gln   Glu   Thr   Met   Tyr   Met   Thr   Val   Ser   Ile   Ile   Asp   Arg
                              20                      25                              30

Phe   Met   Gln   Asn   Asn   Cys   Val   Pro   Lys   Lys   Met   Leu   Gln   Leu   Val   Gly
```

|   |   |   |   | 35 |   |   |   |   | 40 |   |   |   |   | 45 |   |
|---|---|---|---|---|---|---|---|---|---|---|---|---|---|---|---|
| Val | Thr | Ala | Met | Phe | Ile | Ala | Ser | Lys | Tyr | Glu | Glu | Met | Tyr | Pro | Pro |
|   |   |   | 50 |   |   |   | 55 |   |   |   | 60 |   |   |   |   |
| Glu | Ile | Gly | Asp | Phe | Ala | Phe | Val | Thr | Asp | Asn | Thr | Tyr | Thr | Lys | His |
| 65 |   |   |   |   | 70 |   |   |   |   | 75 |   |   |   |   | 80 |
| Gln | Ile | Arg | Gln | Met | Glu | Met | Lys | Ile | Leu | Arg | Ala | Leu | Asn | Phe | Gly |
|   |   |   |   | 85 |   |   |   |   | 90 |   |   |   |   | 95 |   |
| Leu | Gly | Arg | Pro | Leu | Pro | Leu | His | Phe | Leu | Arg | Arg | Ala | Ser | Lys | Ile |
|   |   |   | 100 |   |   |   |   | 105 |   |   |   |   | 110 |   |   |
| Gly | Glu | Val | Asp | Val | Glu | Gln | His | Thr | Leu | Ala | Lys | Tyr | Leu | Met | Glu |
|   |   |   | 115 |   |   |   |   | 120 |   |   |   |   | 125 |   |   |
| Leu | Thr | Met | Leu | Asp | Tyr | Asp | Met | Val | His | Phe | Pro | Pro | Ser | Gln | Ile |
|   | 130 |   |   |   |   | 135 |   |   |   |   | 140 |   |   |   |   |
| Ala | Ala | Gly | Ala |   |   |   |   |   |   |   |   |   |   |   |   |
| 145 |   |   |   |   |   |   |   |   |   |   |   |   |   |   |   |

( 2 ) INFORMATION FOR SEQ ID NO:7:

( i ) SEQUENCE CHARACTERISTICS:
        ( A ) LENGTH: 148 amino acids
        ( B ) TYPE: amino acid
        ( C ) STRANDEDNESS: Not Relevant
        ( D ) TOPOLOGY: linear ( i i ) MOLECULE TYPE: peptide ( v i ) ORIGINAL SOURCE:
        ( A ) ORGANISM: S. pombe ( x i ) SEQUENCE DESCRIPTION: SEQ ID NO:7:

| Met | Arg | Gly | Ile | Leu | Thr | Asp | Trp | Leu | Ile | Glu | Val | His | Ser | Arg | Phe |
|---|---|---|---|---|---|---|---|---|---|---|---|---|---|---|---|
| 1 |   |   |   | 5 |   |   |   |   | 10 |   |   |   |   | 15 |   |
| Arg | Leu | Leu | Pro | Glu | Thr | Leu | Phe | Leu | Ala | Val | Asn | Ile | Ile | Asp | Arg |
|   |   |   | 20 |   |   |   |   | 25 |   |   |   |   | 30 |   |   |
| Phe | Leu | Ser | Leu | Arg | Val | Cys | Ser | Leu | Asn | Lys | Leu | Gln | Leu | Val | Gly |
|   |   |   | 35 |   |   |   |   | 40 |   |   |   |   | 45 |   |   |
| Ile | Ala | Ala | Leu | Phe | Ile | Ala | Ser | Lys | Tyr | Glu | Glu | Val | Met | Cys | Pro |
|   |   |   | 50 |   |   |   | 55 |   |   |   | 60 |   |   |   |   |
| Ser | Val | Gln | Asn | Phe | Val | Tyr | Met | Ala | Asp | Gly | Gly | Tyr | Asp | Glu | Glu |
| 65 |   |   |   |   | 70 |   |   |   |   | 75 |   |   |   |   | 80 |
| Glu | Ile | Leu | Gln | Ala | Glu | Arg | Tyr | Ile | Leu | Arg | Val | Leu | Glu | Phe | Asn |
|   |   |   |   | 85 |   |   |   |   | 90 |   |   |   |   | 95 |   |
| Leu | Ala | Tyr | Pro | Asn | Pro | Met | Asn | Phe | Leu | Arg | Arg | Ile | Ser | Lys | Ala |
|   |   |   | 100 |   |   |   |   | 105 |   |   |   |   | 110 |   |   |
| Asp | Phe | Tyr | Asp | Ile | Gln | Thr | Arg | Thr | Val | Ala | Lys | Tyr | Leu | Val | Glu |
|   |   |   | 115 |   |   |   |   | 120 |   |   |   |   | 125 |   |   |
| Ile | Gly | Leu | Leu | Asp | His | Lys | Leu | Leu | Pro | Tyr | Pro | Pro | Ser | Gln | Gln |
|   | 130 |   |   |   |   | 135 |   |   |   |   | 140 |   |   |   |   |
| Cys | Ala | Ala | Ala |   |   |   |   |   |   |   |   |   |   |   |   |
| 145 |   |   |   |   |   |   |   |   |   |   |   |   |   |   |   |

( 2 ) INFORMATION FOR SEQ ID NO:8:

( i ) SEQUENCE CHARACTERISTICS:
        ( A ) LENGTH: 152 amino acids
        ( B ) TYPE: amino acid
        ( C ) STRANDEDNESS: Not Relevant
        ( D ) TOPOLOGY: linear ( i i ) MOLECULE TYPE: peptide (vi) ORIGINAL SOURCE:
    (A) ORGANISM: S. cerevisiae (xi) SEQUENCE DESCRIPTION: SEQ ID NO:8:

| Met | Arg | Phe | Leu | Ile | Phe | Asp | Phe | Ile | Met | Tyr | Cys | His | Thr | Arg | Leu |
| 1 | | | | 5 | | | | | 10 | | | | | 15 | |

| Asn | Leu | Ser | Thr | Ser | Thr | Leu | Phe | Leu | Thr | Phe | Thr | Ile | Leu | Asp | Lys |
| | | | 20 | | | | | 25 | | | | | 30 | | |

| Tyr | Ser | Ser | Arg | Phe | Ile | Ile | Lys | Ser | Tyr | Asn | Tyr | Gln | Leu | Leu | Ser |
| | | 35 | | | | | 40 | | | | | 45 | | | |

| Leu | Thr | Ala | Leu | Trp | Ile | Ser | Ser | Lys | Phe | Trp | Asp | Ser | Lys | Asn | Arg |
| | 50 | | | | | 55 | | | | | 60 | | | | |

| Met | Ala | Thr | Leu | Lys | Val | Leu | Gln | Asn | Leu | Cys | Cys | Asn | Gln | Tyr | Ser |
| 65 | | | | | 70 | | | | | 75 | | | | | 80 |

| Ile | Lys | Gln | Phe | Thr | Thr | Met | Glu | Met | His | Leu | Phe | Lys | Ser | Leu | Asp |
| | | | | 85 | | | | | 90 | | | | | 95 | |

| Trp | Ser | Ile | Cys | Gln | Ser | Ala | Thr | Phe | Asp | Ser | Tyr | Ile | Asp | Ile | Phe |
| | | | 100 | | | | | 105 | | | | | 110 | | |

| Leu | Phe | Gln | Ser | Thr | Ser | Pro | Leu | Ser | Pro | Gly | Val | Val | Leu | Ser | Ala |
| | | 115 | | | | | 120 | | | | | 125 | | | |

| Pro | Leu | Glu | Ala | Phe | Ile | Gln | Gln | Lys | Leu | Ala | Leu | Leu | Asn | Asn | Ala |
| | 130 | | | | | 135 | | | | | 140 | | | | |

| Ala | Gly | Thr | Ala | Ile | Asn | Lys | Ser |
| 145 | | | | | 150 | | |

METHOD FOR DIAGNOSING NEOPLASIA BY DETECTING EXPRESSION OF PRAD1 CYCLIN

This application is a division of application Ser. No. 07/667,711, filed Mar. 11, 1991, (status: pending).

Partial funding for the work described herein was provided by the U.S. Government, which has certain rights in the invention.

BACKGROUND OF THE INVENTION

This invention relates to the field of cyclins.

The cyclins are a class of eukaryotic proteins that were originally identified by their cyclic accumulation and destruction at defined points in embryonic cell cycles (Evans et al., Cell 33:389–396, 1983). They bind to and are essential for activation of cdc2 protein kinase (reviewed in Murray et al., Science 246:614–621, 1989; Nurse, Nature 344:503–508, 1990; Draetta et al., Cell 56:829–838, 1989). At present, the cyclins can be divided into three families on the basis of their kinetics of oscillation across the cell cycle, their amino acid sequences, and, in some cases, genetic experiments in yeast that determine when their functions are needed (reviewed in Nurse, 1990; Nasmyth, Cell 63:1117–1120, 1990; Westendorf, J. Cell Biol. 108:1431–1444, 1989). The B-type "mitotic" cyclins drive cells into mitosis; their sequences are conserved from yeast to human (Nurse, 1990; Westencorf et al., 1989; and Pines et al., Cell 58:833–846, 1989). The A-type cyclins, which are less well understood, may act earlier in the cell cycle (Minshull et al., EMBO J. 9:2865–2875, 1990; Pines et al., Nature 346:760–763, 1990; Swenson et al., Cell 47:861–870, 1986). The recently described CLNs (or "G1 cyclins") of budding yeast are thought to perform analogous functions by interacting with cdc2 homologues at START, driving cells into S-phase (Nasmyth, 1990). A, B, and CLN cyclins may act as stage-specific regulators of progress across the cell cycle by conferring selective substrate specificity upon cdc2 kinase (Minshull et al., 1990) or by selectively targeting cdc2 to different intracellular compartments.

SUMMARY OF THE INVENTION

The invention features a novel cyclin, prad1, and an isolated DNA (termed PRAD1) which encodes it. This DNA may e single-stranded or double-stranded, and may be genomic DNA, cDNA, or synthetic DNA. It may be identical to a naturally-occurring Prad1sequence (such as human PRAD1 CDNA, SEQ ID NO:1) or may differ from such sequence by the deletion, addition, or substitution of one or more nucleotides. By "isolated" is meant that the DNA is free of the coding sequences of genes that, in the naturally-occurring genome of the organism from which the DNA of the invention is derived, immediately flank the gene encoding prad1. Included within the term prad is human prad1and any homolog of human prad1(i.e., from another animal species, or a genetically altered version of a naturally-occurring prad1which exhibits a biological activity similar to that of the naturally-occurring protein) encoded by a DNA which is capable of hybridizing (1) under stringent hybridization conditions (Sambrook et al., Molecular Cloning: A Laboratory Manual, 2nd edn., Cold Spring Harbor, N.Y., 1989: herein incorporated by reference) to a single-stranded probe consisting of a segment of at least eight (preferably 18–40) nucleotides of human Prad1cDNA (SEQ ID NO:1) or human Prad1genomic DNA, or (2) under less stringent conditions (e.g., washing at 2×SSC, at 40°C.) to a probe consisting of a segment of at least 40 (preferably 200–5000) nucleotides of human Prad1cDNA (SEQ ID NO:1) or human Prad1genomic DNA. Also within the invention are peptide fragments of a naturally-occurring prad1, which fragments are at least six amino acids in length and preferably 10–50 amino acids; and single-stranded DNA or RNA probes (preferably radioactively labelled) containing at least 8 nucleotides of, but less than all of, human Prad1-encoding RNA, human Prad1cDNA (SEQ ID NO:1) or human PRAD1 genomic DNA, and preferably between 10 and 5000 bases. Such DNA or RNA probes may be used in a diagnostic method which includes the steps of obtaining a nucleic acid sample from an animal suspected of having a given neoplastic condition (or from a known tumor); contacting the nucleic acid sample with a single-stranded DNA or RNA probe capable of hybridizing to the Prad1homolog of the species to which the animal belongs; and detecting the level of hybridization of the probe with the nucleic acid sample, such level being diagnostic for the neoplastic condition. Two examples of neoplastic conditions that may be diagnosed by this method include centrocytic lymphomas, which appear to express abnormally high levels of Prad1mRNA, and those breast cancers which are characterized by a high degree of amplification of Prad1DNA.

The DNA sequence of the invention, which may be under the transcriptional control of a heterologous promoter (defined as a promoter sequence other than the naturally-occurring promoter of the gene encoding prad1), may be incorporated into a vector (such as a phage) and thereby introduced into a cell. Included within the invention is a eukaryotic or prokaryotic cell (or an essentially homogeneous population of such cells) containing (and preferably capable of expressing) a recombinant DNA molecule encoding prad1: that is, a cell into which (or into an ancestor of which) has been introduced, by means of genetic engineering, a DNA molecule encoding prad1, resulting in that DNA molecule's being positioned adjacent to a DNA sequence to which it is not naturally adjacent (e.g., the prad1-encoding sequence is integrated into the genome of such cell). The prad1protein of the invention may be produced by culturing such cells and recovering prad1from the cells, or from their medium. Alternatively, DNA or mRNA encoding prad1may be combined with a standard in vitro expression system to produce prad1. Prad1so produced can be utilized in combination with a pharmacologically-acceptable carrier to promote wound healing in an animal, or can be used to promote proliferation of an animal cell by treating the cell with a proliferation-inducing amount of the protein of the invention (for example, by transfecting the cell with DNA encoding prad1so that the cell itself produces such a proliferation-inducing amount of prad1). Alternatively, the prad1(or an antigenic fragment thereof, determined by standard methodology) can be used to raise polyclonal or monoclonal antibodies capable of forming immune complexes with prad1, and thus useful as a diagnostic for certain neoplastic conditions characterized by abnormally high levels of prad1expression. The method of using such an antibody as a diagnostic would include the steps of obtaining a sample of a tissue of an animal suspected of having a such a neoplastic condition (e.g., certain lymphomas or breast cancers); contacting the sample with the antibody; and detecting the level of immune complexes formed by the antibody, such level being diagnostic for the neoplastic condition.

Also within the invention is a transgenic non-human vertebrate animal (preferably a mammal such as a rodent, e.g., a mouse) bearing a transgene (i.e., a piece of DNA which is artificially inserted into an embryonic cell, and becomes a part of the genome of the animal which develops from that cell) which includes a DNA sequence encoding prad1, and any cells or cell lines derived from such an animal. A transgenic animal is an animal having cells that contain a transgene, which transgene was introduced into the animal, or an ancestor of the animal, at an embryonic stage. If the embryonic stage is a single-cell stage, then all nucleated cells of the animal will carry the transgene. The particular prad1encoded by the transgene may be endogenous to the species of the transgenic animal, or may be that of a different species (e.g., human). By using a Prad1together with an appropriate promoter, a transgenic animal which readily develops neoplasias in a selected organ or tissue type will result, making such animal useful as a model for studying cancer in that organ or tissue.

Other features and advantages of the invention will be apparent from the following detailed description, and from the claims.

DETAILED DESCRIPTION

The drawings are first described.

DRAWINGS

FIG. 1 is a Southern blot of Msp1-digested DNA probed with the 5' PTH gene probe (lanes 1, 2) and 3' PTH gene probe (lanes 3, 4).

FIGS. 2A and 2B are a diagrammatic representation of (2A) the normal PTH gene, and (2B) the two fragments resulting from the rearrangement in tumor M.

FIG. 3 is diagrammatic representation of the D11S287 region, indicating known restriction sites and the locations of the 500 bp fragment, the 1.6 kb XhoI fragment, and Probe B.

FIGS. 6A–6G are a representation of the nucleotide sequence and predicted amino acid sequence of human PRAD1 (SEQ ID NO:1) cDNA.

FIG. 7 is an illustration of sequence homology between the "cyclin box" region of human prad1and the corresponding regions of some A-type, B-type, and G1 cyclins.

Figure 1:
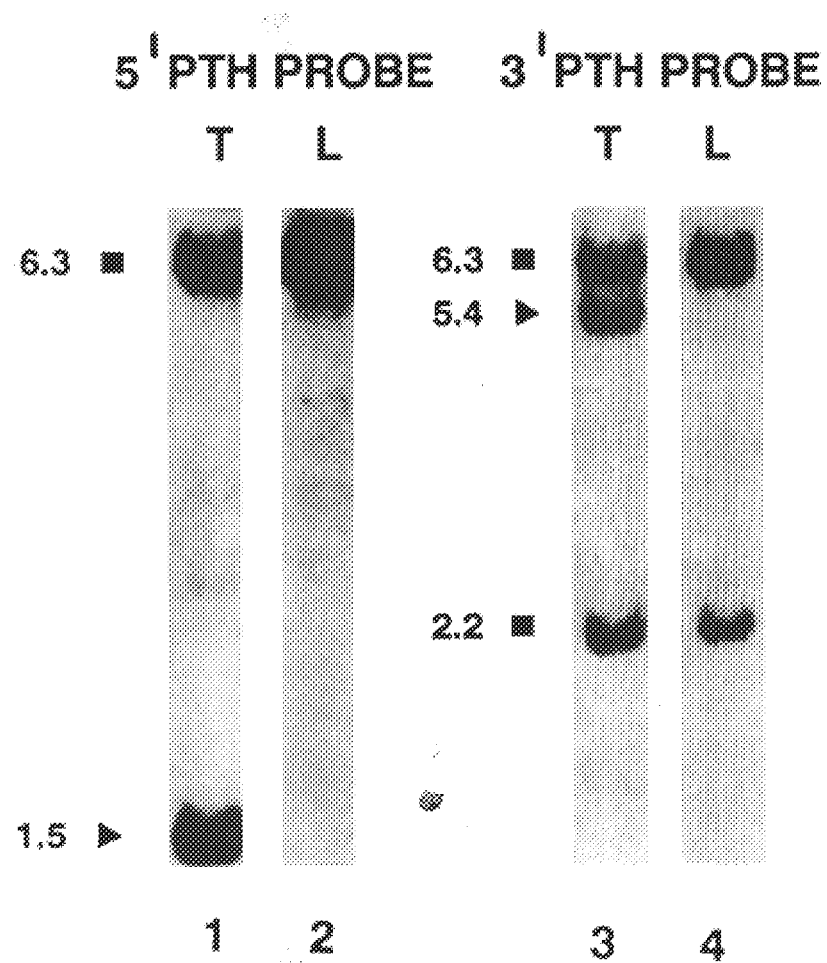

FIGS. 10A–10D an analysis of the biological activity of recombinant human prad1.

dentification of Human PRAD1

Previous studies on DNA from cells of a benign parathyroid adenoma (reported in Arnold et al., J. Clin. Invest. 83:2034–2040, 1989) revealed evidence of a DNA rearrangement involving the parathyroid hormone (PTH) chromosomal locus (at chromosome 11, band p15) and a segment of DNA (identified as Human Genome Database assignment D11S287) which normally maps to chromosome 11, band q13. It is now known that (a) although a number of previously-identified oncogenes (including INT-2 and HST-1), as well as the translocation breakpoint marker BCL-1 and possibly the gene for multiple endocrine neoplasia type I (MEN-I), map to the 11q13 region, the so-called D11S287 locus rearranged in at least some parathyroid adenomas is distinct from these previously-described markers; (b) D11S287 mRNA, while detectable in all tissues analyzed, is significantly overexpressed in those parathyroid adenomas which have a 11q13/11p15 chromosomal rearrangement, and also in certain lymphomas (notably centrocytic lymphomas) characterized by rearrangement of the BCL-1 locus; and (c) the D11S287 locus is amplified and expressed in many squamous cell and mammary carcinomas. This evidence suggests that D11S287 (also referred to herein as human PRAD1, for parathyroid adenoma) is a newly-identified oncogene which figures in a variety of types of neoplasms.

Cloning Human Prad1CDNA (SEQ ID NO:1)

Human Prad1cDNA (SEQ ID NO: 1) has been cloned and sequenced by the methods described in detail below, yielding the sequence shown in FIG. 6. The longest open reading frame, starting at the first ATG codon, encodes a predicted protein of 295 amino acids ($M_r$ 33,729). Screening the Genbank peptide database with this sequence reveals significant homology only to members of the cyclin family, with greatest similarity in the region conserved among cyclins, ranging from 19.1% to 33.6% identity, and 44.1% to 59.2% similarity. The human Prad1(SEQ ID NO:1) protein (prad1) has significant sequence similarities to all three types of cyclins (A, B, and CLN cyclins), but cannot readily be assigned to any one type. This suggests that prad1may represent a new and different cyclin family member.

Prad1Expression

Prad1nRNA is expressed in many tissues and is highly conserved across species (FIG. 7). As with other cyclin mRNAs expressed in human cells (Pines et al., Cell 58:833–846, 1989; Pines et al., Nature 346:760–763, 1990), human Prad1MRNA levels vary across the cell cycle (FIG. 9), consistent with but not proving a role in cell cycle regulation. The peak in Prad1mRNA levels occurs late in the cell cycle or in G1.

Biological Activity of Recombinant Human Prad1Protein

Bacterially expressed recombinant human prad1, produced as described in detail below, was used to further investigate the link between human Prad1and the cyclins. Cyclins are known to form complexes with $p_{34}^{cdc2}$ protein kinase, leading to its activation which can be assayed using exogenous histone H1 as a substrate. In addition, cyclin/$p34^{cdc2}$ complexes can be purified by exploiting the ability of beads linked to $p13^{suc1}$, another cell cycle protein, to avidly bind $p34^{cdc2}$ and, in turn, co-purify any proteins complexed with $p34^{cdc2}$ (Draetta et al., Cell 56:829–838, 1989). When recombinant human prad1was added to clam embryo interphase cell lysates (which lack endogenous cyclins and contain inactive $p34^{cdc2}$), both $p34^{cdc2}$ and prad1were bound by $p13^{suc1}$-beads (FIG. 10). As prad1does not bind to protein A-Sepharaose beads, its binding to $p13^{suc1}$-beads is most likely due to its interaction with $p34^{cdc2}$ or a closely related protein. Furthermore, kinase activity was induced by the addition of the human Prad1 (SEQ ID No:1) in vitro translation product to interphase lysates (FIG. 10). This kinase activity was lower than that seen with cyclin A. Cyclin B provided a negative control; for reasons not yet understood, our cyclin B translation product was not capable of activating $p34^{cdc2}$ in this type of assay. The difference between the activities induced by cyclin A and human prad1may be specific to this clam assay system, or may reflect a genuine difference between the functions of, or the substrate specificities conferred by, cyclin A vs. human prad1.

Use

Both prad1 and a nucleotide encoding prad1 are useful for the preparation of diagnostic tools for the classification and/or prognosis of lymphomas, breast cancers, and squamous cell cancers, as well as other cancers characterized by a high level of expression and/or amplification of the Prad1 gene. For example, prad1 or an antigenic peptide fragment of prad1 could be used in accordance with standard methods (see, e.g., Harlow et al., Antibodies: A Laboratory Manual, Cold Spring Harbor Laboratory, Cold Spring Harbor, N.Y., 1988; Yanaihara et al., U.S. Pat. No. 4,855,406; and Slamon et al., U.S. Pat. No. 4,918,162; all of which are herein incorporated by reference) to raise polyclonal or monoclonal antibodies capable of forming immune complexes with prad1, and useful for detecting abnormally high levels of prad1 in a given tissue sample. Similarly, a hybridization probe prepared from a segment of at least 8 (and preferably greater than 250) nucleotides of human Prad1-encoding RNA, human PRAD1 cDNA (SEQ ID NO:1) or human Prad1 genomic DNA may be employed as a means for determining the number of copies of Prad1 present in the genomic DNA of a given sample, or the level of Prad1 mRNA expressed in cells of such sample.

The nucleic acids of the invention may also be used therapeutically. Oligonucleotides which are antisense to human Prad1 mRNA (or which express RNA that is antisense to human Prad1 mRNA) may be synthesized to serve as an anticancer therapy in those cases diagnosed as having a rearrangement or amplification of human PRAD1: such oligonucleotides would be introduced into tumor cells in vivo as a means to reduce production of prad1 in such cells, and thereby to reduce neoplastic growth induced by an overabundance of prad1. (See, for example, Weinberg et al., U.S. Pat. No. 4,740,463, herein incorporated by reference.) By linking a Prad1 sequence to a selected tissue-specific promoter or enhancer and introducing by standard methods (e.g., as described by Leder et al., U.S. Pat. No. 4,736,866, herein incorporated by reference) the resultant hybrid gene into an animal embryo at an early developmental stage (e.g., the fertilized oocyte stage), a transgenic animal which expresses elevated levels of prad1 in the selected tissue (e.g., breast, squamous cell, B-lymphoid cell, parathyroid, and others) can be produced. The form of Prad1 utilized can be one which encodes a prad1 similar to that of the animal species used, or it can encode the prad1 homolog of a different species (e.g., human). Such an animal would be useful as an in vivo model for neoplastic disease in the selected tissue. In addition, cells derived from. such a transgenic animal may be used to establish an immortal cell line that retains at least some of its differentiated characteristics while proliferating indefinitely in vitro. Alternatively, one could stably transfect primary cells (e.g., a type that has proven difficult to maintain in culture, such as pituitary cells) with a Prad1 gene linked to an appropriate promoter (e.g., the metallothionin promoter) which ensures high levels of expression of the gene, and thereby establish an immortal cell line derived from such primary cells. Prad1 sequences may be particularly useful in this regard because overexpression of Prad1 (at least in parathyroid tissues) appears to trigger the proliferation of normally quiescent cells without causing them to completely lose their differentiated phenotype.

EXPERIMENTAL DATA

The DNA abnormality in parathyroid tumor M was initially characterized by Southern analysis of MspI digests using probes specific for the 5' and 3' regions in the PTH gene (see below), which revealed a unique, tumor-specific band. FIG. 1 illustrates these Southern blots of tumor M (T) and peripheral blood leukocyte (L) DNA pairs. MspI-digested DNA was probed with the 51 PTH gene probe (lanes 1, 2) and 3' PTH gene probe (lanes 3, 4). Squares indicate the normal gene (6.3 kb); arrows indicate the rearranged allele (1.5 kb in lane 1, 5.4 kb in lane 3). There is an MspI site within the DNA to which the 31 probe hybridizes (see FIG. 2a); therefore, a smaller band (2.2 kb) representing the most 3' section of the normal PTH gene is present in lanes 3 and 4. The intensities of the bands representing the abnormal allele were approximately equal to those representing the normal allele. Thus, in tumor M, as in tumor Y (Arnold et al., 1989), a clonal rearrangement of the PTH gene has occurred: in every tumor cell, one of the two alleles of the PTH gene remains normal but the other is disrupted. FIG. 2(a) illustrates the normal PTH gene, with the positions of its three exons (Vasicek et al., Proc. Natl. Acad. Sci. USA 80:2127–2131, 1983), the 5' and 3' probes used in mapping and cloning, and the MspI sites indicated. In comparison, FIG. 2(b) shows the two fragments resulting from the rearrangement in tumor M: one consists of the 5' PTH gene sequences plus juxtaposed non-PTH DNA (stippled area), while the other consists of 3' PTH gene sequences plus juxtaposed non-PTH DNA (cross-hatched area). In each fragment, the location of the breakpoint is shown by a diagonal line. The locations of several restriction enzyme sites, determined by Southern blot analysis of tumor DNA, are indicated: EcoRI (R), BamHI (B), HindIII (H), XhoI (X), SstI (S), MspI (M). The locations and sizes of the 1.5 kb and 5.4 kb rearranged MspI fragments, (shown in FIG. 1) are indicated above each fragment. Below each fragment, lines ending in arrow tips depict the 1.5 kb and 16 kb cloned tumor DNA fragments. Analysis with multiple additional restriction enzymes indicated that the gene is separated into two parts, with the breakpoint located in the first intron (FIG. 2b). Consequently, upstream regulatory elements and the first, non-coding exon in the 5' fragment are separated from the coding sequences in the 3' fragment. Each PTH gene fragment remains internally intact (within the limits of sensitivity of restriction mapping), but has become juxtaposed to non-PTH DNA.

To identify the rearranged non-PTH DNA (shaded and cross-hatched areas in FIG. 2b), two DNA fragments containing PTH gene sequences plus breakpoint-adjacent DNA were cloned from tumor M DNA. One was a 16 kb BamHI fragment containing approximately 8 kb of non-PTH gene DNA adjacent to 8 kb of 3' PTH gene sequences (FIG. 2b). Genomic Southern blots of normal DNA probed with subclones spanning most of the 8 kb of non-PTH DNA showed diffuse smears that did not yield to attempts at competition with excess human DNA (Sealy et al., 1985). This indicated that the non-PTH DNA in the 16 kb fragment contained sequences highly repeated in the human genome, and precluded its chromosomal localization.

We also cloned a 1.5 kb EcoRI fragment containing approximately 1 kb of the PTH gene's 5' region plus 500 bp of juxtaposed non-PTH DNA (FIG. 2b). Probing normal human DNA blots with the subcloned 500 bp fragment demonstrated that it contained single-copy DNA; in situ hybridization and analysis of somatic cell hybrids revealed that the 500 bp fragment's normal chromosomal location is 11q13.

Hybridization of the 500 bp breakpoint-adjacent DNA fragment to an RNA blot of six parathyroid adenomas, including two with PTH gene rearrangements, was negative. To identify transcribed sequences near the breakpoint that could have been affected by the rearrangement, we walked along the chromosome by probing a normal human genomic library with the 500 bp subcloned fragment. We obtained a bacteriophage clone with a 14 kb insert, but Northern blot analyses revealed no hybridization of subclones spanning the entire insert. Mapping of the 14 kb insert showed that the 500 bp fragment was at one end, and demonstrated that the adjacent cloned DNA had a restriction map identical to that of the genomic DNA juxtaposed to tumor M's rearranged 5' PTH gene fragment. (Compare FIGS. 2b and 3). At the other end of the 14 kb insert was a 1.6 kb XhoI fragment (FIG. 3) identical in size to an XhoI fragment 1 kb from tumor Y's D11S287 breakpoint (Arnold et al., 1989). We subcloned these two independent 1.6 kb XhoI fragments (one from the above normal phage clone and one from a tumor Y-derived clone) and used them sequentially to probe blots of normal human genomic DNA digested with 7 restriction enzymes. With every enzyme, the two probes hybridized to precisely comigrating fragments. In addition, restriction maps of the two 1.6 kb fragments themselves were identical for all 6 enzymes used. Thus, the 1.6 kb XhoI fragment linked tumor M's breakpoint-adjacent DNA with that of tumor Y (D11S287), confirming that the 11q13 breakpoints in the two adenomas are both in the D11S287 region, separated by 15 kb. The composite restriction map of the unrearranged D11S287 region is shown in FIG. 3, in which restriction sites for the enzymes HindIII (H), BamHI (B), EcoRI (E), SacI (S), MspI (M) and XhoI (X) are indicated. The locations of the 500 bp fragment, the 1.6 kb XhoI fragment, and probe B are shown. This map is derived from the maps of the phage clones described above and by Arnold et al. (1989), and Southern blots of DNA from tumors M and Y.

Figure 4:
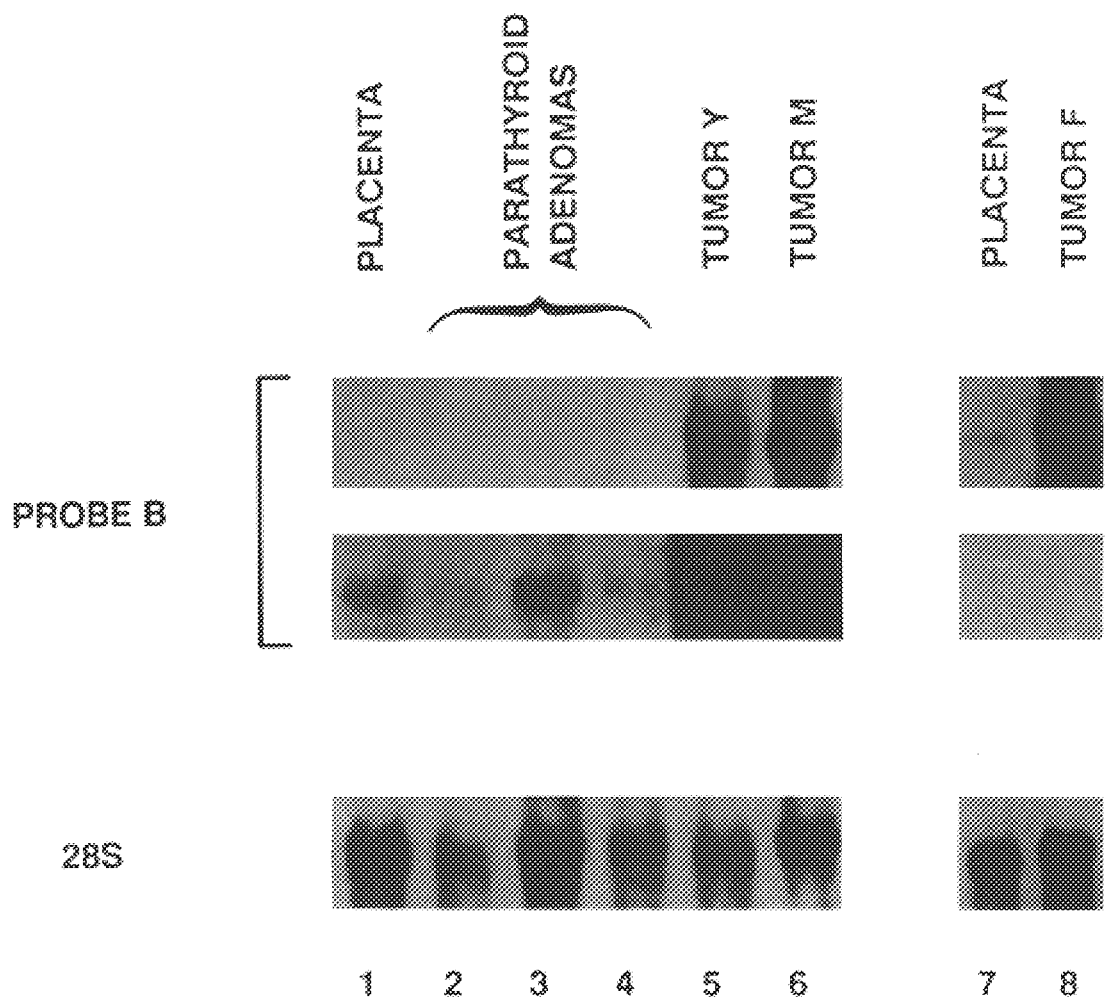
FIG. 4 is a Northern analysis of D11S287 expression in various cell types.

The proximity of the 11q13 breakpoints suggested that the rearrangements could have similar functional consequences. Because none of the DNA between the two tumors' breakpoints is transcribed in parathyroid cells, we looked for transcribed sequences distal to tumor Y's breakpoint. We used fragment B (FIG. 3), a breakpoint-adjacent DNA fragment from tumor Y, to probe a blot containing total RNA from human placenta, several parathyroid adenomas lacking PTH gene rearrangements, and tumors M and Y. We also hybridized probe B to another blot containing total RNA from placenta and from another parathyroid adenoma (tumor F) that was found recently to contain a clonal rearrangement of the PTH and D11S287 loci (Friedman et al., 1990); Southern blotting indicated that tumor F's rearrangement closely resembled tumor Y's. FIG. 4 presents the results of the Northern blots, in which 10 micrograms of total RNA was probed with Probe B (top panels), and with a 28S rRNA probe (bottom panels). Size determination was based on the migration of 28S rRNA. Lanes contain the following samples: lanes 1, 7: placenta; lanes 2, 3, 4: parathyroid adenomas without PTH gene or D11S287 rearrangements; lanes 5, 6, 8: tumors Y, M, and F, respectively; lanes 7 and 8 are a separate Northern filter. The middle panel is a longer exposure of lanes 1–6 in the top panel. In lanes 5 and 8 (tumors Y and F) a faint band was visible, larger than the highly-overexpressed 4.5 kb band, which was not seen in lane 6 (tumor M) (data not shown). Exposure times: top row (probe B): lanes 1–6, 17h; lanes 7 and 8, 12h; Middle row (probe B): all lanes, 52h; Bottom row (28S rRNA): all lanes, 1.5h. An approximately 4.5 kb transcript (slightly smaller than the 28S rRNA band) was seen in all lanes of FIG. 4. However, the intensity of the 4.5 kb band in tumors M, Y and F was roughly 15-fold greater than that in any of the other specimens. We demonstrated that the 4.5 kb band represents polyadenylated RNA by finding its intensity amplified in poly A+ RNA (data not shown).

Parathyroid adenoma M initially was identified as having an abnormal PTH gene during studies of the monoclonality of parathyroid adenomas (tumor 1 in Arnold et al., N. Eng. J. Med. 318:658–662, 1988). All tumor specimens were frozen in liquid nitrogen shortly after surgical removal. Extraction of high molecular weight DNA, restriction enzyme digestion and Southern blotting were performed as previously described (Arnold et al., N. Eng. J. Med., 309:1593–1599, 1983). Total RNA was isolated by the guanidinium thiocyanate/cesium chloride method, electrophoresed on a denaturing formaldehyde-agarose gel, and transferred to nitrocellulose or nylon filters (Sambrook et al., Molecular Cloning, A Laboratory Manual, 2nd edn. Cold Spring Harbor Laboratory Press, Cold Spring Harbor, N.Y., pp. 7.19–7.22, 7.37–7.39, 11.31–11.32, 1989). Hybridization conditions were similar to those used for Southern filters. Blots were washed at high stringency (0.1×SSC, 65°).

PTH gene fragments used as hybridization probes were the 775 bp BglII fragment (5' PTH probe) and the 2.6 kb SstI-EcoRI fragment (3' PTH probe) from pPTHg108 (Igarashi et al., Mol. Cell. Biol. 6:1830–1833, 1986) (FIG. 2a). The 500 bp fragment and probe B (FIG. 3) were subcloned into pUC-18 from the breakpoint-adjacent DNA of the phage clones containing the rearranged PTH gene fragment plus juxtaposed DNA from tumor M (see above), and tumor Y (Arnold et al., 1989), respectively. The 1.6 kb XhoI fragment from the 14 kb insert cloned from the normal human genomic library was also sub-cloned into pUC-18. The 1.6 kb XhoI fragment from tumor Y was subcloned from a Xphage 2001 clone containing the 17 kb HindIII fragment of tumor Y's unrearranged D11S287 allele (Arnold et al., 1989). All the above probes were random-primed and labelled with [$^{32}$P] dATP (Feinberg & Vogelstein, Anal. Biochem. 132:6–13, 1983). The 28S RNA oligonucleotide was end-labelled with [$^{32}$P]dATP (Sambrook et al., 1989) and used to probe the Northern filters to control for the amount of high molecular weight RNA present in each lane.

To clone the rearranged 5' PTH gene fragment (FIG. 2b), an EcoRI library of tumor genomic DNA was constructed using the λZapII vector (Stratagene). This library was screened with the 5' PTH gene probe, and the rearranged allele was distinguished from the normal allele by size, as DNA blots predicted that the rearranged EcoRI fragment would be 1.5 kb in size, and the normal fragment 3.5 kb. One clone containing the rearranged gene was identified in 1×10$^6$ plaques that were screened.

To clone the rearranged 3' PTH gene fragment (FIG. 2b), a BamHI library of tumor genomic DNA was constructed in EMBL-3. Because restriction mapping indicated that both the normal and rearranged 3' PTH BamHI fragments were 16 kb in size, the library was screened with the 3' PTH probe (expected to hybridize to both the normal and rearranged PTH alleles) and then with the 5' PTH probe (expected to hybridize only to the normal allele). One clone containing the rearranged allele was identified in 6.5×10$^3$ plaques screened. As predicted, it contained 8 kb of 3' PTH gene sequences and 8 kb of newly-juxtaposed DNA. Most of this 8 kb was sub-cloned in roughly 2 kb units into pUC-18, and used to probe Southern filters of normal genomic DNA.

Prereassociation was performed by sonicating 1 mg of human placental genomic DNA and incubating it for 10–60 min with 50–100 ng of labelled repeat-containing subcloned DNA. This mix was then hybridized to a Southern filter containing normal human DNA using standard conditions.

The genomic library used to obtain the 14 kb insert was a partial Sau-3a digest of normal human DNA cloned into an EMBL-3 like vector (Clontech).

Chromosomal mapping using human-mouse somatic cell hybrids (Shows et al., Adv. Hum. Genet. 12:341–452, 1982; Shows et al., Somatic Cell Mol. Genet. 10:315–318, 1984); Southern blotting (Naylor et al., J. Exp. Med. 57:1020–1027, 1983); and in situ hybridization (Zabel et al., Cytogenet. Cell Genet. 39:200–205, 1985; Nakai et al., Cytogenet. Cell Genet. 43:215–217, 1986) was performed as previously described.

Figure 5:
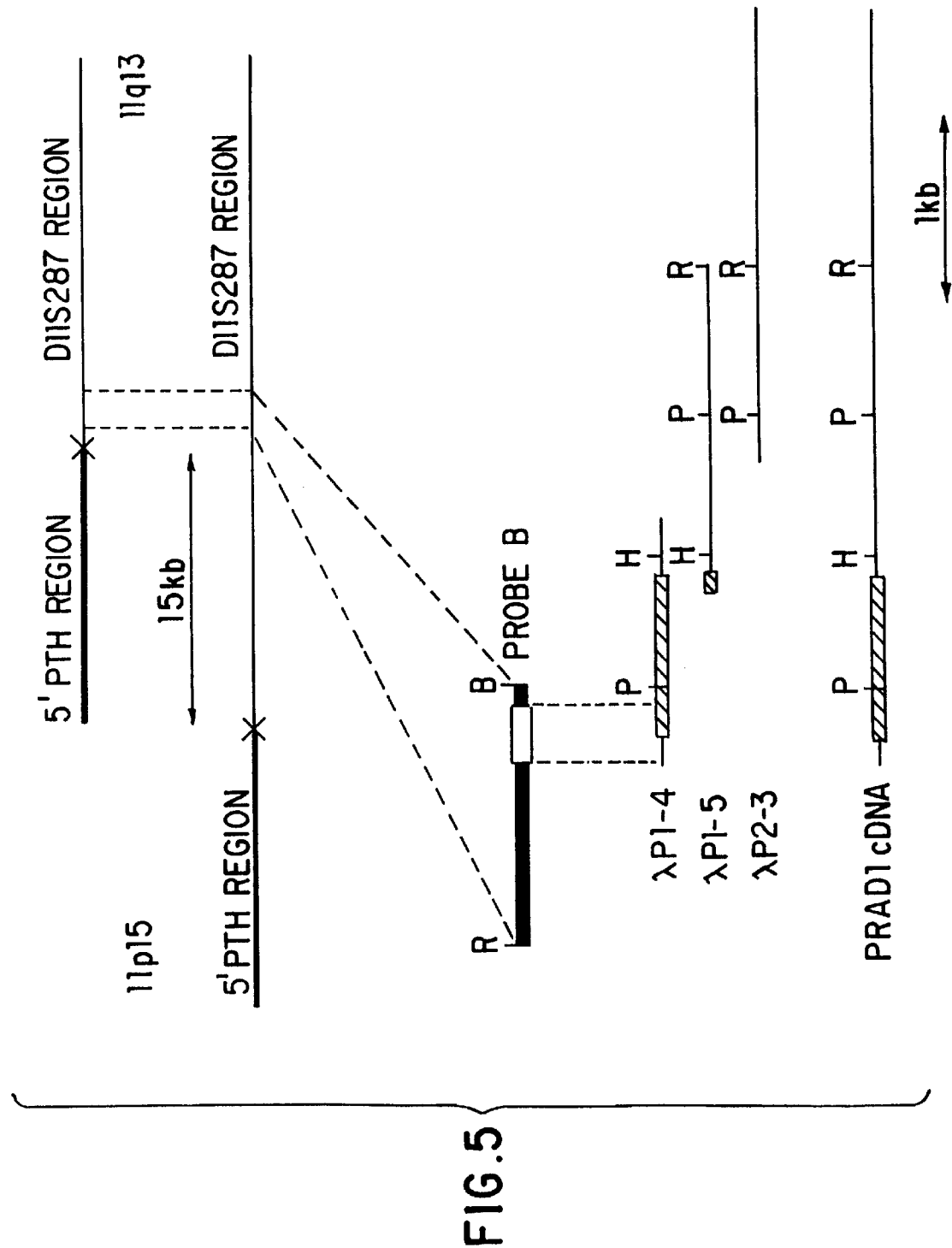
FIG. 5 is a diagrammatic representation of THD11S287 rearrangements in two parathyroid adenomas, and he relative locations of Probe B and a series of cloned cDNA segments.

A λgt11 placental cDNA library (Clontech) was screened with radiolabeled Probe B. A clone denominated XP1–4 and another similar phage clone were isolated. Probe B and the insert of XP1–4 were sequenced. The region of genomic and CDNA overlap was followed in Probe B by a GT splice donor sequence in only one orientation, confirming hybridization data which had suggested transcription in the left to right orientation, as shown in FIG. 5. The next probe was made by polymerase chain reaction amplification of the 3' region of the XP1–4 cDNA insert, and used to rescreen the same library. From $5 \times 10^5$ pfu of this library, one of 16 positive clones, XP1–5, had an insert extending further downstream. The PstI/EcoRI fragment of λP1–5 was then used to rescreen the library, and 12 similar clones, the longest of which was λP2–3, were obtained. The sequence of the insert of λP2–3 revealed polyadenylation signals and a polyA stretch of 16 nucleotides in an appropriate position, consistent with the expected orientation. Standard methods for library screening and probe labeling were used (Davis et al., Basic Methods in Molecular Biology (Elsevier, N.Y., Amsterdam, London, 1986). These clones are illustrated in FIG. 5, together with a schematic representation of PTH/D11S287 rearrangements in two parathyroid adenomas. The 5' PTH region (11p15, thick lines) was juxtaposed to the D11S287 region (11q13, thin lines) in each of these adenomas. The breakpoints in the D11S287 region are 15 kb apart. Genomic Probe B is shown as a darkened box, whose open area represents the first exon of Prad1. Also shown are restriction maps of the inserts of representative overlapping Prad1cDNA clones, XP1–4, XP1–5, and XP2–3; and the deduced restriction map of the Prad1cDNA. The coding region is shown as a crosshatched box. Scale of 1 kb is shown as arrows. Symbols used for restriction sites are: B. BamHI; E, EcoRI; H, HindIII; P, PstI.

The inserts of the clones λP1–4, λP1–5, and λP2–3 shown in FIG. 5, and of other independent clones, were subcloned into pGEM7Zf(+) (Promega). Sequences were obtained using the double-stranded DNA sequencing technique (dideoxy method) with modified T7 DNa polymerase (Sequenase; U.S. Biochemical Corporation), as described by the manufacturer. Several oligonucleotides were synthesized as internal primers to facilitate sequencing. The coding region was sequenced in both orientations and in at least two independent clones. Set forth in FIG. 6 are the nucleotide sequence and predicted. amino acid sequence of human Prad1cDNA (SEQ ID NO:1). Nucleotide numbers are on the right. Nucleotide 3495, shown as W, indicates A or T because the sequences of two independent clones did not agree. Nucleotide 4017 is shown as R, meaning A or G, for the same reason.

FIG. 7 illustrates sequence homology between the "cyclin box" region of the predicted Prad1protein (prad1) and that of A-type cyclins (human and clam cyclin A) (Swenson et al., Cell 47:861–870, 1986, and Wang et al., Nature 343:555–557, 1990); B-type cyclins (human cyclin B and S. pombe cdc13) (Pines et al., Cell 58:833–846, 1989; and Booher et al., EMBO J. 7:2321–2327, 1988), and one S. cerevisiae G1 cyclin (cln3) (Nash et al., EMBO J. 7:43354346, 1988; Cross et al., Mol. Cell. Biol. 8:4675–4684, 1988) Clam cyclin A and S. pombe cdc13 homologies with prad1are representative of those found in their families; cln3 alignes with prad1more closely than does cln1 or 2. Identical amino acids are shown as |. Conservative substitutions are shown as *. Alignment was made with the assistance of the BESTFIT program (Devereux et al., Nucl. Acids Res. 12:387–395, 1984) and conservative amino acids are grouped as follows: D, E, N, Q; H, K, R; A, G, P, S, T; I, L, M, V; F, W, Y. Amino acid numbers are on the right in this Figure.

Figure 8:
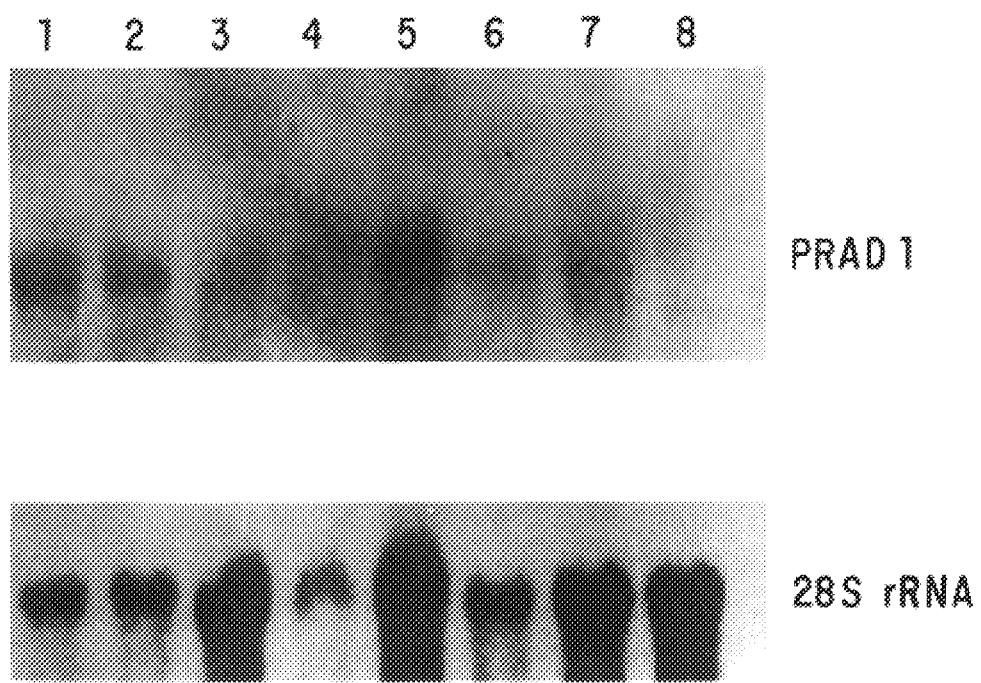
FIG. 8 is a Northern blot analysis of D11S287 [human Prad1(SEQ ID NO:1)] expression in various cell types.
Figure 9A:
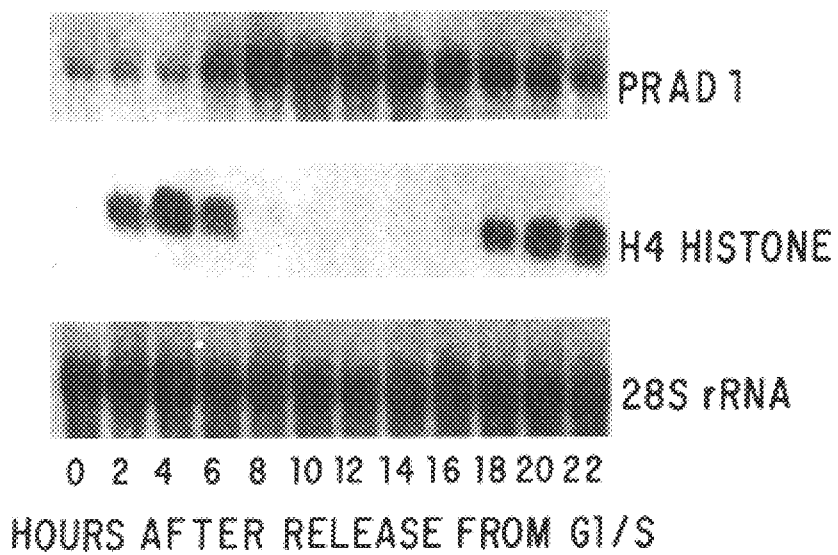
FIGS. 9A and 9B are (9A) a Northern blot analysis of HeLa cell RNA probed with a human Prad1cDNA (SEQ ID NO:1) probe, an H4 histone probe, and 28S rRNA; and (9B) b a graph depicting the results of the Northern blot.
Figure 9B:
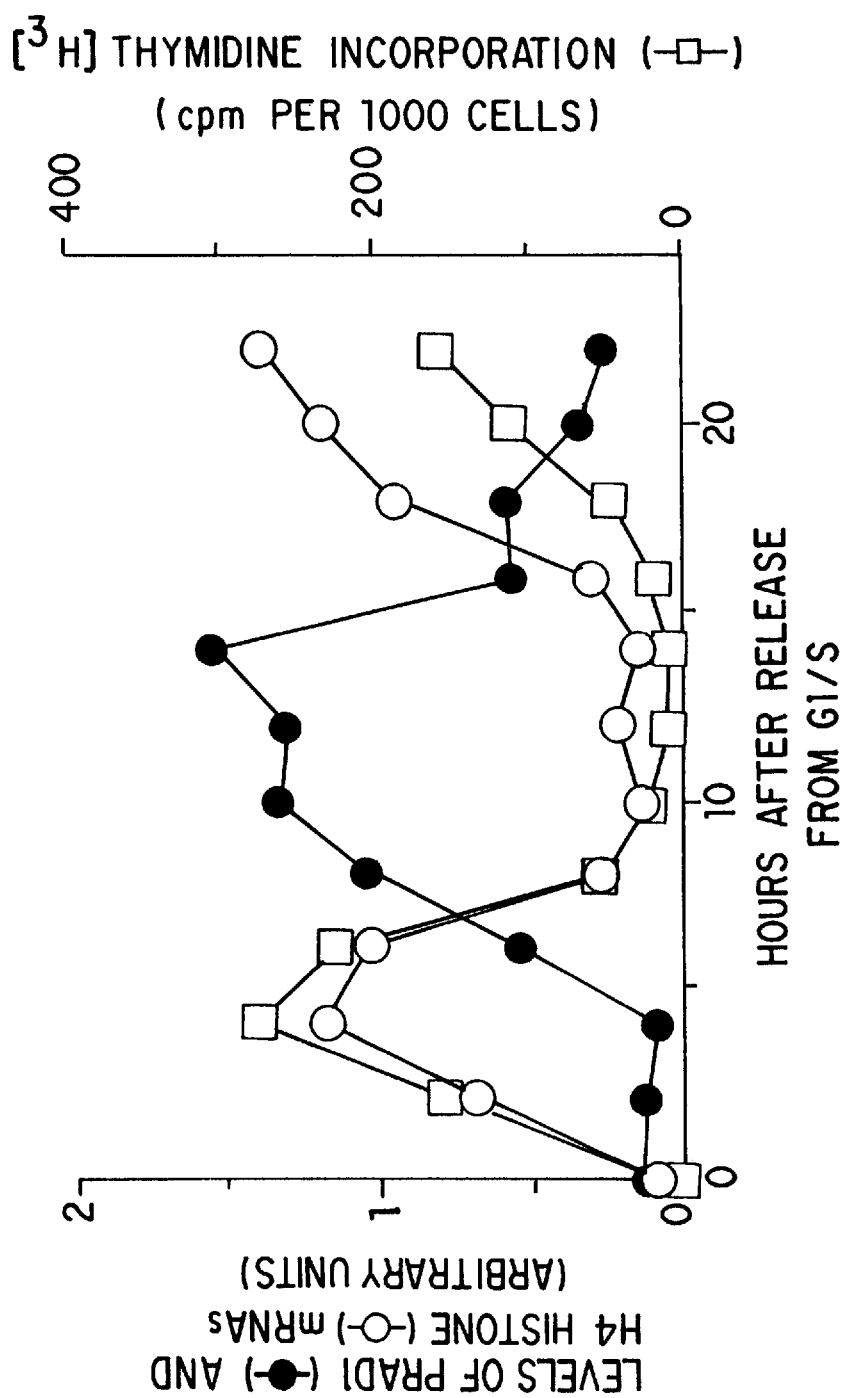
Figure 10A:
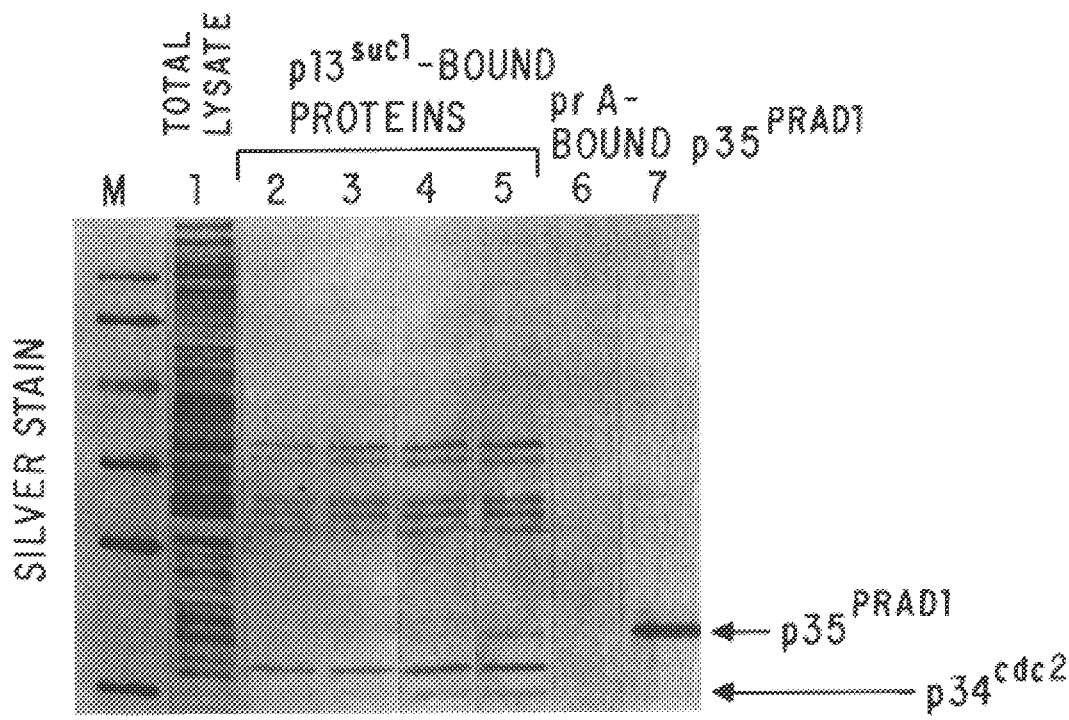
Figure 10B:
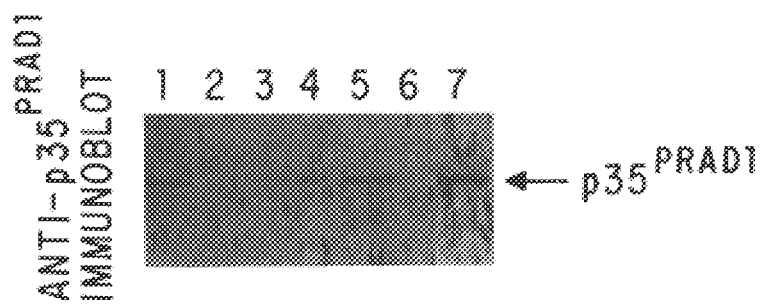
Figure 10C:
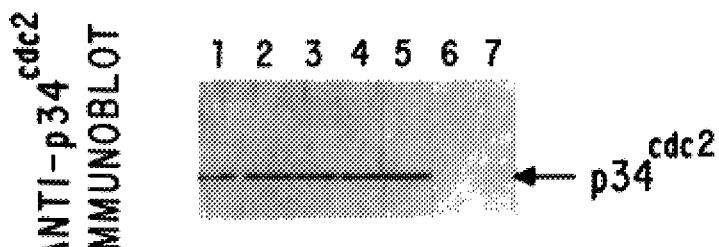
Figure 10D:
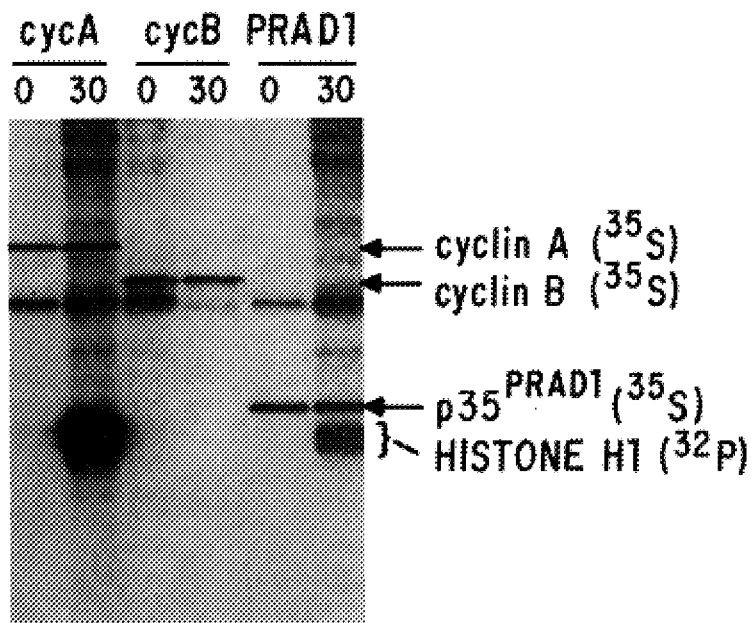

RNAs were prepared for Northern blot analysis from the indicated tissues by standard procedures (Davis et al., 1986). 10 µg total RNA was loaded and separated on an agarose-formaldehyde gel, blotted onto nitrocellulose, and hybridized with Probe B or the 28S rRNA oligonucleotide. The filters were washed at high stringency (0.1×SSC, 60°C.) and autoradiographed. FIG. 8 illustrates a Northern blot analysis of total RNA from human thyroid (lane 1), human placenta (lane 2), bovine parathyroid (lane 3), bovine thyroid (lane 4), bovine lymph node (lane 5), bovine skeletal muscle (lane 6), murine heart (lane 7), and murine liver (lane 8). Prad1RNA (shown in the upper panel) is approximately 4.5 kb in size, slightly smaller than the 28S rRNA; 28S rRNA hybridization is shown in the lower panel. FIG. 9(a) shows a Northern blot analysis of total RNA from HeLa S3 cells after release from G1/S block. Hela S3 cells (American Type Culture Collection), maintained in Dulbecco Modified Eagle Medium (DMEM, GIBCO) with 7% fetal bovine serum (FBS), were synchronized at the G1/S boundary by sequential thymidine-aphidicolin treatment (Heintz, et al., Mol. Cell. Biol. 3:539–550, 1983) with a slight modification. Log-phase cells were incubated in complete medium (DMEM with 7% FBS, penicillin G, and streptomycin) with addition of 2mM thymidine (Sigma) for 12 h. After release from thymidine block by 3 washes with PBS, the cells were incubated for 10 h with 24 µM deoxycytidine (Sigma) and 24 µM thymidine, recovered by trypsinization, counted, and aliquoted equally ($5.0 \times 10^4$ cells/cm$^2$). Incubation with 5 µg/ml aphidicolin (Sigma) for 14 h was followed by release from G1/S block with 4 DMEM washes and incubation in complete medium. [$^3$H] Thymidine (NEN) was added to an aliquot 15 min before each indicated time point; a 30 min incubation and harvesting for trichloroacetic acid (TCA) precipitation followed. RNAs from parallel aliquots were extracted (Chomczynski et al., Anal. Biochem. 162:156–159, 1987) at the indicated times; time zero was just before release from aphidicolin. RNAs (5 µg per lane) were blotted onto nitrocellulose and sequentially hybridized with the Prad1λp1–4 cDNA insert, human H4 histone pF0108X (Pauli et al., Science 236:1308–1311, 1987), and a 28S rRNA oligonucleotide as described above. Human Prad1TRNA is shown in the upper panel of FIG. 9(a); H4 histone mRNA in the middle panel shows the pattern expected in well-synchronized cells (Heintz et al., 1983); and 28S rRNA is shown in the lower panel as a control for RNA loading. In FIG. 9(b) are compared the relative amounts of human PRAD1 mRNA —●—, H4 histone mRNA —○—, and [$^3$H] thymidine incorporation —□—of HeLa S3 cells after release from G1/S block. The signals of the blot shown in FIG. 9(a) were measured by densitometry and normalized to the 28S rRNA to produce the graph of FIG. 9(b).

Clam embryo interphase cell lysates lacking endogenous cyclins were prepared by adding 100 µM emetine during first mitosis, as described previously (Luca et al., J. Cell Biol. 109:1895–1909, 1989), followed by homogenization and centrifugation at 150,000×g. Aliquots of the supernatant were frozen in liquid nitrogen. [$^{35}$S]methionine-labeled prad1was produced in a reticulocyte lysate in vitro translation system (Promega) according to manufacturer's instructions, by using a plasmid (denominated pP1–8) containing the XP1–4 insert in pGEM7Zf(+) (Promega). To produce prad1in *E. coli,* pT4R-1 was constructed by insertion of the XP1–4 insert into the NcoI and BamHI sites of pET-3d (Studier et al., Meth. Enzym. 108:60–89, 1990). BL21(DE3) cells were transformed with pT4R-1, cultured, and treated with 0.4 mM isopropylthio-beta-galactosidase (IPTG) for 3 h to induce prad1expression. The induced product was purified from cell culture as inclusion bodies (Gardella et al., J. Biol. Chem 265:15854–15859, 1990). On SDS-polyacrylamide gels, the apparent sizes of the in vitro translation product and the bacterially-expressed product were the same ($M_r$ 35 kD). Rabbit anti-prad1antisera were raised against a synthetic peptide corresponding to amino acids 9–37 of prad1. Antisera were assayed by immunoprecipitation of the in vitro translation product. Antisera specificity was shown by comparison with normal rabbit serum and by successful competition with the (9–37) peptide (data not shown).

Thawed clam embryo lysate (16.5 μl) and bacterially-expressed prad1(5.5 μl) were mixed and incubated at 18° C. for 30 min before transfer to 4° C., dilution with 4 volumes of buffer A (50 mM Tris pH 7.4, 150 mM NaCl, 5 mM EDTA, 5 mM EGTA, 1 mM ammonium molybdate) and addition of p13$^{suc1}$- or protein A-Sepharose, followed by mixing for 1 h. Beads were then pelleted and washed in buffer A+0.5% Tween-20; in buffer B (50 mM Tris pH 7.4, 1.0M NaCl, 5 mM EDTA, 5 mM EGTA, 1 mM molybdate, 0.5% Tween-20); and finally in buffer A without Tween-20, all at 4°C. Washed beads were boiled in SDS sample buffer for 3 min and the supernatant split into three samples for electrophoresis. Gels were silver stained or blotted onto nitrocellulose filters and reacted with rabbit antibodies generated against bacterially-expressed, full-length *S. pombe* cdc2 protein or prad1peptide as above. Antibody binding was visualized by alkaline phosphatase-linked secondary antibodies, according to the manufacturer's directions (Promega). FIG. 10 demonstrates that prad1 protein added to clam embryo cell lysates binds to p13$^{suc1}$-Sepharose beads and activates histone H1 kinase activity. Bacterially expressed prad1was incubated with a clam embryo interphase lysate lacking endogenous cyclins A and B. The lysates were then mixed with p13$^{suc1}$-or protein A-Sepharose beads. The bound material was eluted, electrophoresed and either silver stained (a) or immunoblotted with anti-prad1 antiserum (b) or anti- cdc2 antiserum (c). Lane M shows molecular weight markers (from top to bottom) of 116, 94, 68, 56, 40, and 31 kD. Lane 1 shows whole clam embryo interphase lysate plus 18 ng prad1protein. Lanes 2, 3, 4, 5, and 6 represent clam embryo lysate to which 0, 18, 45, 225, or 18 ng of prad1, respectively, were added; these mixes were then assayed for material binding to $p_{13}{}^{suc1}$-Sepharose (lanes 2–5) or protein A-Sepharose (lane 6) beads. Lane 7 shows bacterially-expressed prad1. Arrows indicate the positions of prad1and cdc2 marker proteins.

Equal volumes of clam embryo interphase lysate and reticulocyte lysate containing [$^{32}$P]-labeled kinase products were then examined by SDS-PAGE, followed by autoradiography. Synthetic clam cyclins A and B (Westendorf et al., J. Cell Biol. 108:1431–1444; Swenson et al., Cell 47:861–870, 1986) and prad1mRNAs were transcribed and translated as described above. Translation product (3 μl) and clam embryo lysate (3 μl) were mixed. Samples were frozen immediately in liquid nitrogen. The remainder was incubated for 30 min at 18° C. and then frozen. Samples were diluted with 1 volume of ice-cold buffer A, thawed on ice, and mixed with an equal volume of kinase mix (40 nM Hepes pH 7.3, 20mM $MgCl_2$, 10 mM EGTA, 0.2 mg/ml histone H1, 10 μM cAMP-dependent kinase inhibitor (Sigma), 0.5 mCi/ml [λ-$^{32}$P]ATP and incubated at 23° C. for 10 min. Double-strength SDS sample buffer was then added and the entire mix was analyzed by SDS-PAGE followed by autoradiography, as shown in FIG. 10(*d*).

What is claimed is:

1. A method for diagnosing neoplasia by detecting expression level of PRAD1 cyclin comprising:

obtaining a nucleic acid sample from an animal suspected of having a neoplastic condition;

contacting said nucleic acid sample with a single-stranded DNA comprising a segment of a PRAD 1 at least 8 nucleotides in length, said Prad1being the Prad1homolog of the species to which said animal belongs; and detecting the level of hybridization of said single-stranded DNA with said nucleic acid sample, said level being diagnostic for said neoplastic condition.

2. The method of claim 1, wherein said animal is a mammal.

3. The method of claim 2, wherein said mammal is a human.

4. The method of claim 1, wherein said neoplastic condition is breast cancer.

5. The method of claim 1, wherein said neoplastic condition is a lymphoma.

6. The method of claim 1, wherein said neoplastic condition is a squamous cell cancer.

7. The method of claim 1, wherein said neoplastic condition is parathyroid adenoma.

* * * * *

UNITED STATES PATENT AND TRADEMARK OFFICE
CERTIFICATE OF CORRECTION

PATENT NO.    : 5,858,655
DATED         : January 12, 1999
INVENTOR(S)   : Arnold It is certified that error appears in the above-identified patent and that said Letters Patent is hereby corrected as shown below:

<u>Title page, Item [54] and Column 1, lines 1-3,</u>
Please change the title deleting "METHOD FOR DIAGNOSING NEOPLASIA BY DETECTING EXPRESSION OF PRAD1 CYCLIN" and inserting therefor
-- METHOD FOR DIAGNOSING NEOPLASIA BY DETECTING EXPRESSION OF PRAD1 CYCLIN (CYCLIN D1) --.

Signed and Sealed this

Twenty-sixth Day of August, 2003

JAMES E. ROGAN
*Director of the United States Patent and Trademark Office*